(12) United States Patent
Paille et al.

(10) Patent No.: US 9,307,899 B2
(45) Date of Patent: Apr. 12, 2016

(54) PROCESS FOR DETERMINING A PAIR OF PROGRESSIVE OPHTHALMIC LENSES

(71) Applicant: ESSILOR INTERNATIONAL (COMPAGNIE GENERALE D'OPTIQUE), Charenton le Pont (FR)

(72) Inventors: Damien Paille, Charenton le Pont (FR); Benjamin Rousseau, Charenton le Pont (FR); Aude Contet, Charenton le Pont (FR); Isabelle Poulain, Charenton le Pont (FR); Stéphanie Vialet, Charenton le Pont (FR); Farid Karioty, Charenton le Pont (FR)

(73) Assignee: ESSILOR INTERNATIONAL (COMPAGNIE GENERALE D'OPTIQUE), Charenton le Pont (FR)

( * ) Notice: Subject to any disclaimer, the term of this patent is extended or adjusted under 35 U.S.C. 154(b) by 0 days.

(21) Appl. No.: 14/402,276

(22) PCT Filed: Jun. 28, 2013

(86) PCT No.: PCT/EP2013/063602
§ 371 (c)(1),
(2) Date: Nov. 19, 2014

(87) PCT Pub. No.: WO2014/001490
PCT Pub. Date: Jan. 3, 2014

(65) Prior Publication Data
US 2015/0103312 A1    Apr. 16, 2015

(30) Foreign Application Priority Data

Jun. 29, 2012 (EP) .................................. 12305772

(51) Int. Cl.
| | | |
|---|---|---|
| G02C 7/06 | (2006.01) | |
| A61B 3/00 | (2006.01) | |
| G02C 7/02 | (2006.01) | |
| G02C 13/00 | (2006.01) | |

(52) U.S. Cl.
CPC .............. *A61B 3/0025* (2013.01); *G02C 7/025* (2013.01); *G02C 7/027* (2013.01); *G02C 7/061* (2013.01); *G02C 7/063* (2013.01); *G02C 13/005* (2013.01); *G02C 2202/04* (2013.01)

(58) Field of Classification Search
CPC .......... G01C 7/02; G01C 7/024; G01C 7/027; G01C 7/028; G01C 7/06; G01C 7/061; G01C 7/063; G01C 7/065; G01C 7/066; G01C 7/068; G02C 2202/12
USPC ............. 351/159.01, 159.41, 159.42, 159.43, 351/159.46, 159.74
See application file for complete search history.

(56) References Cited

U.S. PATENT DOCUMENTS

| | | | | |
|---|---|---|---|---|
| 4,056,311 | A * | 11/1977 | Winthrop ............... | G02C 7/063 351/159.42 |
| 5,790,226 | A | 8/1998 | Pollak | |
| 2010/0097570 | A1 | 4/2010 | Katzman et al. | |
| 2011/0317128 | A1* | 12/2011 | Guilloux ............... | G02C 7/025 351/246 |

FOREIGN PATENT DOCUMENTS

| | | |
|---|---|---|
| EP | 2 369 403 | 9/2011 |
| FR | 2 894 687 | 6/2007 |
| FR | 2 894 688 | 6/2007 |

OTHER PUBLICATIONS

R.C. Oldfield, "The Assessment and Analysis of Handedness: The Edinburgh Inventory", Neuropsychologia, vol. 9, pp. 97-113, 1971, Pergamon Press.

* cited by examiner

*Primary Examiner* — Huy K Mai
(74) *Attorney, Agent, or Firm* — Cozen O'Connor

(57) ABSTRACT

A process for determining a pair of personalized progressive ophthalmic lenses. and a computer program product associated to these processes. Right-handed persons and left-handed persons behave very differently when executing certain near vision tasks, such as writing on a sheet of paper. However, current lens designs do not take into account these behavior differences. The comfort of wearing a pair of ophthalmic lenses can be improved for the wearer for whom the lenses are intended by adapting his near vision according to his handedness.

15 Claims, 16 Drawing Sheets

PROCESS FOR DETERMINING A PAIR OF PROGRESSIVE OPHTHALMIC LENSES

RELATED APPLICATIONS

This application is a U.S. National Phase Application under 35 USC 371 of International Application PCT/EP2013/063602 filed Jun. 28, 2013.

This application claims the priority of European application No. 12305772.1 filed Jun. 29, 2012, the entire content of which is hereby incorporated by reference.

FIELD OF THE INVENTION

The invention relates to a process for determining a pair of progressive ophthalmic lenses. The invention further relates to a process for determining a pair of personalized progressive ophthalmic lenses, a pair of progressive ophthalmic lenses and a computer program product associated to these processes.

BACKGROUND OF THE INVENTION

A wearer may be prescribed a positive or negative optical power correction. For presbyopic wearers, the value of the power correction is different for far vision and near vision, due to the difficulties of accommodation in near vision. The prescription thus comprises a far-vision power value and an addition representing the power increment between far vision and near vision. The addition is qualified as prescribed addition. Ophthalmic lenses suitable for presbyopic wearers are multifocal lenses, the most suitable being progressive multifocal lenses.

The inventors have found that right-handed persons and left-handed persons behave very differently when executing certain near vision tasks, such as writing on a sheet of paper.

However, current lens designs do not take into account these behaviour differences.

SUMMARY OF THE INVENTION

An object of the present invention is to improve the comfort of wearing a pair of ophthalmic lenses for the wearer for whom the lenses are intended by adapting his near vision according to his handedness, also called manual laterality or simply laterality hereinafter.

A process for determining a pair of progressive ophthalmic lenses is thus proposed. The process comprises:
  determining a prescribed far vision mean power for each lens of the pair;
  determining a prescribed addition for each lens of the pair;
  determining laterality of a wearer;
  defining a temporal side and a nasal side on each lens of the pair;
  defining, on each lens being worn and for each gaze direction, a refractive power and a module of resulting astigmatism, each gaze direction corresponding to a lowering angle and to an azimuth angle;
  defining a proximate vision gaze direction for each lens of the pair;
  defining, for each lens of the pair, a temporal half-width field of refractive power as the angular distance, at constant lowering angle, between the proximate vision gaze direction and a gaze direction on the temporal side of the lens where the refractive power reaches the value of the prescribed far vision mean power plus three quarters of the prescribed addition;
  defining, for each lens of the pair, a nasal half-width field of refractive power as the angular distance, at constant lowering angle, between the proximate vision gaze direction and a gaze direction on the nasal side of the lens where the refractive power reaches the value of the prescribed far vision mean power plus three quarters of the prescribed addition;
  defining, for each lens of the pair, a temporal half-width field of module of resulting astigmatism as the angular distance, at constant lowering angle, between the proximate vision gaze direction and a gaze direction on the temporal side of the lens where the module of resulting astigmatism reaches the value of one quarter of the prescribed addition;
  defining, for each lens of the pair, a nasal half-width field of module of resulting astigmatism as the angular distance, at constant lowering angle, between the proximate vision gaze direction and a gaze direction on the nasal side of the lens where the module of resulting astigmatism reaches the value of one quarter of the prescribed addition.

The ratio of the difference over the sum of temporal and nasal half-width fields of refractive power and/or the ratio of the difference over the sum of temporal and nasal half-width fields of module of resulting astigmatism are determined for each lens of the pair based on the laterality of the wearer.

In an embodiment, if the laterality of the wearer is determined to be left-handed, the ratio of the difference over the sum of temporal and nasal half-width fields of refractive power is set substantially to 0 for each lens of the pair and/or the ratio of the difference over the sum of temporal and nasal half-width fields of module of resulting astigmatism is set substantially to 0 for each lens of the pair.

In an embodiment, if the laterality of the wearer is determined to be left-handed, the ratio of the difference over the sum of temporal and nasal half-width fields of refractive power is set to a value less than or equal substantially to 0 for the right-eye lens and/or the ratio of the difference over the sum of temporal and nasal half-width fields of module of resulting astigmatism is set to a value less than or equal substantially to 0 for the right-eye lens, and the ratio of the difference over the sum of temporal and nasal half-width fields of refractive power is set to a value greater than or equal substantially to 0 for the left-eye lens and/or the ratio of the difference over the sum of temporal and nasal half-width fields of module of resulting astigmatism is set to a value greater than or equal substantially to 0 for the left-eye lens.

In an embodiment, if the laterality of the wearer is determined to be right-handed, the ratio of the difference over the sum of temporal and nasal half-width fields of refractive power may be set to a value greater than or equal substantially to 0 for the right-eye lens and/or the ratio of the difference over the sum of temporal and nasal half-width fields of module of resulting astigmatism may be set to a value greater than or equal substantially to 0 for the right-eye lens, and the ratio of the difference over the sum of temporal and nasal half-width fields of refractive power is set to a value less than or equal substantially to 0 for the left-eye lens and/or the ratio of the difference over the sum of temporal and nasal half-width fields of module of resulting astigmatism is set to a value less than or equal substantially to 0 for the left-eye lens.

In an embodiment, the sum of the ratio of the difference over the sum of temporal and nasal half-width fields of refractive power for the right-eye lens and the ratio of the difference over the sum of temporal and nasal half-width fields of refractive power for the left-eye lens is set substantially to 0.

The sum of the ratio of the difference over the sum of temporal and nasal half-width fields of module of resulting astigmatism for the right-eye lens and the ratio of the difference over the sum of temporal and nasal half-width fields of module of resulting astigmatism for the left-eye lens may be set substantially to 0.

An aspect of the invention relates to a process for determining a pair of personalized progressive ophthalmic lenses, comprising:
  determining a prescribed far vision mean power for each lens of the pair;
  determining prescribed addition for each lens of the pair;
  measuring a useful near vision zone of a wearer and measuring an inclination of the useful near vision zone with respect to an horizontal line;
  determining a temporal side and a nasal side on each lens of the pair;
  defining, on each lens being worn and for each gaze direction, a refractive power and module of resulting astigmatism, each gaze direction corresponding to a lowering angle and to an azimuth angle;
  defining a proximate vision gaze direction for each lens of the pair;
  defining, for each lens of the pair, a temporal half-width field of refractive power as the angular distance, at constant lowering angle, between the proximate vision gaze direction and a gaze direction on the temporal side of the lens where the refractive power reaches the value of the prescribed far vision mean power plus three quarters of the prescribed addition;
  defining, for each lens of the pair, a nasal half-width field of refractive power as the angular distance, at constant lowering angle, between the proximate vision gaze direction and a gaze direction on the nasal side of the lens where the refractive power reaches the value of the prescribed far vision mean power plus three quarters of the prescribed addition;
  defining, for each lens of the pair, a temporal half-width field of module of resulting astigmatism as the angular distance, at constant lowering angle, between the proximate vision gaze direction and a gaze direction on the temporal side of the lens where the module of resulting astigmatism reaches the value of one quarter of the prescribed addition;
  defining, for each lens of the pair, a nasal half-width field of module of resulting astigmatism as the angular distance, at constant lowering angle, between the proximate vision gaze direction and a gaze direction on the nasal side of the lens where the module of resulting astigmatism reaches the value of one quarter of the prescribed addition.

The ratio of the difference over the sum of temporal and nasal half-width fields of refractive power and/or the ratio of the difference over the sum of temporal and nasal half-width fields of module of resulting astigmatism are determined for each lens of the pair based on the measured inclination of the useful near vision zone of the wearer.

The process may comprise a further step of determining a head/eye behaviour of the wearer and wherein the ratio of the difference over the sum of temporal and nasal half-width fields of refractive power and/or the ratio of the difference over the sum of temporal and nasal half-width fields of module of resulting astigmatism are further determined for each lens of the pair based on the head/eye behaviour of the wearer.

The proximate vision gaze direction may be defined, for each lens of the pair, as the gaze direction where the refractive power reaches the prescribed far vision mean power plus 100% of the prescribed addition for said lens of the pair.

Alternatively, the proximate vision gaze direction may be defined, for each lens of the pair, as the gaze direction where the refractive power reaches the prescribed far vision mean power plus 85% of the prescribed addition for said lens of the pair.

Another aspect of the invention also relates to a pair of progressive ophthalmic lenses intended for a right-handed wearer, each lens of the pair having a prescribed far vision mean power and a prescribed addition and comprising a temporal side and a nasal side and a proximate vision control point defined on the front surface, each lens of the pair having, when being worn and for each gaze direction, a refractive power and a module of resulting astigmatism, each gaze direction corresponding to a lowering angle and to an azimuth angle. The right-eye lens has:
  a ratio of the difference over the sum of temporal and nasal half-width fields of refractive power value greater than or equal substantially to 0; and/or
  a ratio of the difference over the sum of temporal and nasal half-width fields of module of resulting astigmatism greater than or equal substantially to 0, while the left-eye lens has:
  a ratio of the difference over the sum of temporal and nasal half-width fields of refractive power value less than or equal substantially to 0 lens; and/or
  a ratio of the difference over the sum of temporal and nasal half-width fields of module of resulting astigmatism less than or equal substantially to 0,
with:
  a temporal half-width field of refractive power defined for each lens of the pair as the angular distance, at constant lowering angle, between the proximate vision control point and the point on the temporal side of the lens where the refractive power reaches the value of the prescribed far vision mean power plus three quarters of the addition;
  a nasal half-width field of refractive power defined for each lens of the pair as the angular distance, at constant lowering angle, between the proximate vision control point and the point on the nasal side of the lens where the refractive power reaches the value of the prescribed far vision mean power plus three quarters of the addition;
  a temporal half-width field of module of resulting astigmatism defined for each lens of the pair as the angular distance, at constant lowering angle, between the proximate vision control point and the point on the temporal side of the lens where the module of resulting astigmatism reaches the value of one quarter of the addition;
  a nasal half-width field of module of resulting astigmatism defined for each lens of the pair as the angular distance, at constant lowering angle, between the proximate vision control point and the point on the nasal side of the lens where the module of resulting astigmatism reaches the value of one quarter of the addition.

Further, for respectively each lens of the pair, $\Delta \leq 10\%$, with
$\Delta = 100 * abs(Max\_Asr\_N - Max\_Asr\_T)/Max(Max\_Asr\_N; Max\_Asr\_T)$,
  abs: absolute value,
  Max_Asr_N: maximum value of resulting astigmatism found over an area of the lens defined by all gaze directions which are comprised:
    within the nasal area of the lens, and
    within a zone centered on the gaze direction passing through the PRP (Prism reference point) and containing all gaze directions $(\alpha,\beta)$ respecting the following inequality $(\alpha^2+\beta^2)^{1/2} \leq 40°$, Max_Asr_T: maximum value of resulting astigmatism found over an area of the lens defined by all gaze directions which are comprised:
within the temporal area of the lens, and
within a zone centered on the gaze direction passing through the PRP
(Prism reference point) and containing all gaze directions $(\alpha,\beta)$ respecting the following inequality $(\alpha^2+\beta^2)^{1/2} \leq 40°$, Max(x;y): whichever value of x and y is higher.

The proximate vision control may be defined, for each lens of the pair, as the point on the front surface intersecting the gaze direction where the refractive power reaches the prescribed far vision mean power plus 100% of the prescribed addition for said lens of the pair.

Alternatively, the proximate vision control point may be defined, for each lens of the pair, as the point on the front surface intersecting the gaze direction where the refractive power reaches the prescribed far vision mean power plus 85% of the prescribed addition for said lens of the pair.

Yet another aspect of the invention also relates to a computer program product comprising one or more stored sequences of instructions accessible to a processor and which, when executed by the processor, causes the processor to carry out the steps of a process as defined above.

Further features and advantages of the invention will appear from the following description of embodiments of the invention, given as non-limiting examples, with reference to the accompanying drawings listed hereunder.

Figure 1:
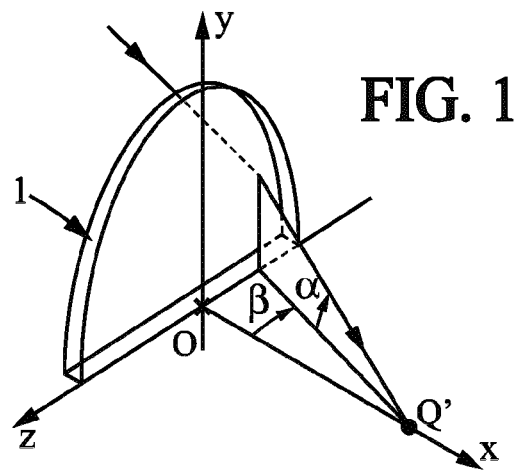
FIGS. 1 and 2 show, diagrammatically, optical systems of eye and lens.

It can be appreciated that elements in the figures are illustrated for simplicity and clarity and have not necessarily been drawn to scale. For example, the dimensions of some of the elements in the figures may be exaggerated relatively to other elements to help improving the understanding of the embodiments of the present invention.

DETAILED DESCRIPTION OF PREFERRED EMBODIMENTS

A process for determining a pair of progressive ophthalmic lenses is proposed. This process enables to adapt the near vision zones according to the laterality of the wearer, thus resulting in an increased comfort for the wearer, particularly when performing near vision tasks.

A progressive lens comprises two non-rotationally symmetrical aspheric surfaces, for instance but not limited to, progressive surface, regressive surface, toric or atoric surfaces.

As is known, a minimum curvature $CURV_{min}$ is defined at any point on an aspherical surface by the formula:

$$CURV_{min} = \frac{1}{R_{max}}$$

where $R_{max}$ is the local maximum radius of curvature, expressed in meters and $CURV_{min}$ is expressed in dioptres.

Similarly, a maximum curvature $CURV_{max}$ can be defined at any point on an aspheric surface by the formula:

$$CURV_{max} = \frac{1}{R_{min}}$$

where $R_{min}$ is the local minimum radius of curvature, expressed in meters and $CURV_{max}$ is expressed in dioptres.

It can be noticed that when the surface is locally spherical, the local minimum radius of curvature $R_{min}$ and the local maximum radius of curvature $R_{max}$ are the same and, accordingly, the minimum and maximum curvatures $CURV_{min}$ and $CURV_{max}$ are also identical. When the surface is aspherical, the local minimum radius of curvature $R_{min}$ and the local maximum radius of curvature $R_{max}$ are different.

From these expressions of the minimum and maximum curvatures $CURV_{min}$ and $CURV_{max}$, the minimum and maximum spheres labeled $SPH_{min}$ and $SPH_{max}$ can be deduced according to the kind of surface considered.

When the surface considered is the object side surface, the expressions are the following:

$$SPH_{min} = (n-1) * CURV_{min} = \frac{n-1}{R_{max}} \text{ and}$$

$$SPH_{max} = (n-1) * CURV_{max} = \frac{n-1}{R_{min}}$$

where n is the index of the constituent material of the lens.

If the surface considered is an eyeball side surface, the expressions are the following:

$$SPH_{min} = (1-n) * CURV_{min} = \frac{1-n}{R_{max}} \text{ and}$$

$$SPH_{max} = (1-n) * CURV_{max} = \frac{1-n}{R_{min}}$$

where n is the index of the constituent material of the lens.

As it is known, a mean sphere $SPH_{mean}$ at any point on an aspherical surface can also be defined by the formula:

$$SPH_{mean} = \frac{1}{2}(SPH_{min} + SPH_{max})$$

The expression of the mean sphere therefore depends on the surface considered:
if the surface is the object side surface, $$SPH_{mean} = \frac{n-1}{2}\left(\frac{1}{R_{min}} + \frac{1}{R_{max}}\right)$$

if the surface is an eyeball side surface, $$SPH_{mean} = \frac{1-n}{2}\left(\frac{1}{R_{min}} + \frac{1}{R_{max}}\right)$$

A cylinder CYL is also defined by the formula $CYL = |SPH_{max} - SPH_{min}|$.

The characteristics of any aspherical face of the lens may be expressed by means of the local mean spheres and cylinders. A surface can be considered as locally aspherical when the cylinder is at least 0.25 diopters.

For an aspherical surface, a local cylinder axis $\gamma_{AX}$ may further be defined.

The cylinder axis $\gamma_{AX}$ is the angle of the orientation of the maximum curvature $CURV_{max}$ with relation to a reference axis and in the chosen direction of rotation. In the TABO convention, the reference axis is horizontal (the angle of this reference axis is 0°) and the direction of rotation is counter-clockwise for each eye, when looking to the wearer ($0° \leq \gamma_{AX} \leq 180°$). An axis value for the cylinder axis $\gamma_{TAX}$ of +45° therefore represents an axis oriented obliquely, which when looking to the wearer, extends from the quadrant located up on the right to the quadrant located down on the left.

A surface may thus be locally defined by a triplet constituted by the maximum sphere $SPH_{max}$, the minimum sphere $SPH_{min}$ and the cylinder axis $\gamma_{AX}$. Alternatively, the triplet may be constituted by the mean sphere $SPH_{mean}$, the cylinder CYL and the cylinder axis $\gamma_{AX}$.

Figure 4:
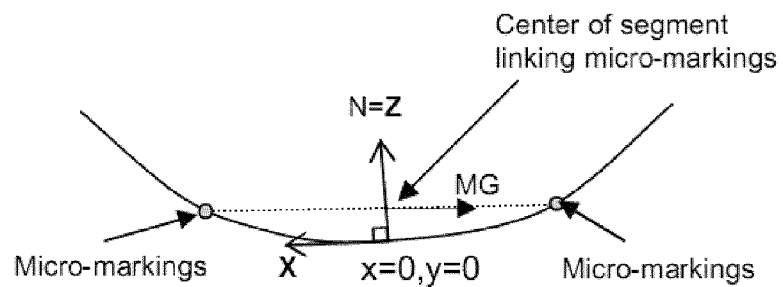
FIGS. 4 and 5 show referentials defined with respect to micro-markings, for a surface bearing micro-markings and for a surface not bearing the micro-markings respectively.
Figure 5:
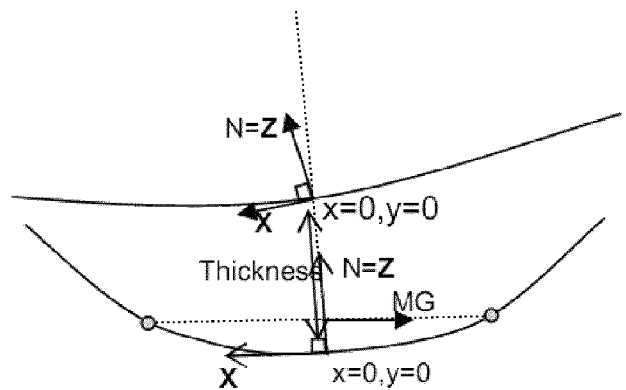

Whenever a lens is characterized by reference to one of its aspherical surfaces, a referential is defined with respect to micro-markings as illustrated in FIGS. 4 and 5, for a surface bearing micro-markings and for a surface not bearing the micro-markings respectively.

Progressive lenses comprise micro-markings that have been made mandatory by the harmonized standard ISO 8990-2. Temporary markings may also be applied on the surface of the lens, indicating positions of control points on the lens, such as a control point for far vision, a control point for near vision, a prism reference point and a fitting cross for instance. If the temporary markings are absent or have been erased, it is always possible for a skilled person to position the control points on the lens by using a mounting chart and the permanent micro-markings.

The micro-markings also make it possible to define referential for both surfaces of: the lens.

FIG. 4 shows the referential for the surface bearing the micro-markings. The center of the surface (x=0, y=0) is the point of the surface at which the normal N to the surface intersect the center of the segment linking the two micro-markings. MG is the collinear unitary vector defined by the two micro-markings. Vector Z of the referential is equal to the unitary normal (Z=N); vector Y is equal to the vector product of Z by MG; vector X of the referential is equal to the vector product of Y by Z. {X, Y, Z} thereby form a direct orthonormal trihedral. The center of the referential is the center of the surface x=0 mm, y=0 mm.

FIG. 5 shows the referential for the surface opposite to the surface bearing the micro-markings. The center of this second surface (x=0, y=0) is the point at which the normal N intersecting the center of the segment linking the two micro-markings on the first surface intersects the second surface. Referential of the second surface is constructed the same way as the referential of the first surface, i.e. vector Z is equal to the unitary normal of the second surface; vector Y is equal to the vector product of Z by MG; vector X is equal to the vector product of Y by Z. The center of the referential of the surface is also x=0 mm, y=0 mm.

Similarly, on a semi-finished lens blank, standard ISO 10322-2 requires micro-markings to be applied. The center of the aspherical surface of a semi-finished lens blank can therefore be determined as well as a referential as described above.

Moreover, a progressive multifocal lens may also be defined by optical characteristics, taking into consideration the situation of the person wearing the lenses.

Figure 2:
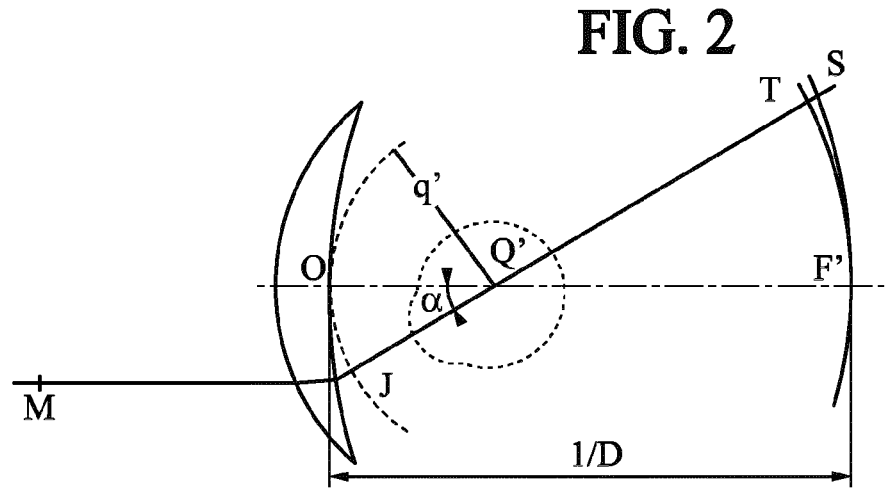

FIGS. 1 and 2 are diagrammatic illustrations of optical systems of eye and lens, thus showing the definitions used in the description. More precisely, FIG. 1 represents a perspective view of such a system illustrating parameters $\alpha$ and $\beta$ used to define a gaze direction. FIG. 2 is a view in the vertical plane parallel to the antero-posterior axis of the wearer's head and passing through the center of rotation of the eye in the case when the parameter $\beta$ is equal to 0.

The center of rotation of the eye is labeled Q'. The axis Q'F', shown on FIG. 2 in a dot-dash line, is the horizontal axis passing through the center of rotation of the eye and extending in front of the wearer—that is the axis Q'F' corresponding to the primary gaze view. This axis cuts the aspherical surface of the lens on a point called the fitting cross, which is present on lenses to enable the positioning of lenses in a frame by an optician. The point of intersection of the rear surface of the lens and the axis Q'F' is the point O. O can be the fitting cross if it is located on the rear surface. An apex sphere, of center Q', and of radius q', which is tangential to the rear surface of the lens in a point of the horizontal axis. As examples, a value of radius q' of 25.5 mm corresponds to a usual value and provides satisfying results when wearing the lenses.

A given gaze direction—represented by a solid line on FIG. 1—corresponds to a position of the eye in rotation around Q' and to a point J (see FIG. 2) of the apex sphere; the angle $\beta$ is the angle formed between the axis Q'F' and the projection of the straight line Q'J on the horizontal plane comprising the axis Q'F'; this angle appears on the scheme on FIG. 1. The angle $\alpha$ is the angle formed between the axis Q'J and the projection of the straight line Q'J on the horizontal plane comprising the axis Q'F'; this angle appears on the scheme on FIGS. 1 and 2. A given gaze view thus corresponds to a point J of the apex sphere or to a couple ($\alpha, \beta$). The more the value of the lowering gaze angle is positive, the more the gaze is lowering and the more the value is negative, the more the gaze is rising.

In a given gaze direction, the image of a point M in the object space, located at a given object distance, is formed between two points S and T corresponding to minimum and maximum distances JS and JT, which would be the sagittal and tangential local focal lengths. The image of a point in the object space at infinity is formed, at the point F'. The distance D corresponds to the rear frontal plane of the lens.

Ergorama is a function associating to each gaze direction the usual distance of an object point. Typically, in far vision following the primary gaze direction, the object point is at infinity. In near vision, following a gaze direction essentially corresponding to an angle $\alpha$ of the order of 35° and to an angle $\beta$ of the order of 5° in absolute value towards the nasal side, the object distance is of the order of 30 to 50 cm. For more details concerning a possible definition of an ergorama, U.S. Pat. No. 6,318,859 may be considered. This document describes an ergorama, its definition and its modeling method. For a method of the invention, points may be at infinity or not. Ergorama may be a function of the wearer's ametropia.

Using these elements, it is possible to define a wearer optical power and astigmatism, in each gaze direction. An object point M at an object distance given by the ergorama is considered for a gaze direction ($\alpha,\beta$). An object proximity ProxO is defined for the point M on the corresponding light ray in the object space as the inverse of the distance MJ between point M and point J of the apex sphere:

$$ProxO = 1/MJ$$

This enables to calculate the object proximity within a thin lens approximation for all points of the apex sphere, which is used for the determination of the ergorama. For a real lens, the object proximity can be considered as the inverse of the distance between the object point and the front surface of the lens, on the corresponding light ray.

For the same gaze direction ($\alpha,\beta$), the image of a point M having a given object proximity is formed between two points S and T which correspond respectively to minimal and maximal focal distances (which would be sagittal and tangential focal distances). The quantity Prox I is called image proximity of the point M:

$$ProxI = \frac{1}{2}\left(\frac{1}{JT} + \frac{1}{JS}\right)$$

The optical power is also called refractive power

By analogy with the case of a thin lens, it can therefore be defined, for a given gaze direction and for a given object proximity, i.e. for a point of the object space on the corresponding light ray, an optical power Pui as the sum of the image proximity and the object proximity.

$$Pui = ProxO + ProxI$$

With the same notations, an astigmatism Ast is defined for every gaze direction and for a given object proximity as:

$$Ast = \left|\frac{1}{JT} - \frac{1}{JS}\right|$$

This definition corresponds to the astigmatism of a ray beam created by the lens.

Possible definitions of the optical power and the astigmatism of the lens, in the wearing conditions, can thus be calculated as explained in the article by B. Bourdoncle et al., entitled "Ray tracing through progressive ophthalmic lenses", 1990 International Lens Design Conference, D. T. Moore ed., Proc. Soc. Photo. Opt. Instrum. Eng. Standard wearing conditions are to be understood as the position of the lens with relation to the eye of a standard wearer, notably defined by a pantoscopic angle of $-8°$, a lens-pupil distance of 12 mm, a pupil-eye rotation center of 13.5 mm and a wrap angle of 0°. The pantoscopic angle is the angle in the vertical plane between the optical axis of the spectacle lens and the visual axis of the eye in the primary position, usually taken to be the horizontal. The wrap angle is the angle in the horizontal plane between the optical axis of the spectacle lens and the visual axis of the eye in the primary position, usually taken to be the horizontal. Other conditions may be used. Wearing conditions may be calculated from a ray-tracing program, for a given lens. Further, the optical power and the astigmatism may be calculated so that the prescription is either fulfilled at the reference points (i.e control points in far vision) and for a wearer wearing his spectacles in the wearing conditions or measured by a frontofocometer.

Figure 3:
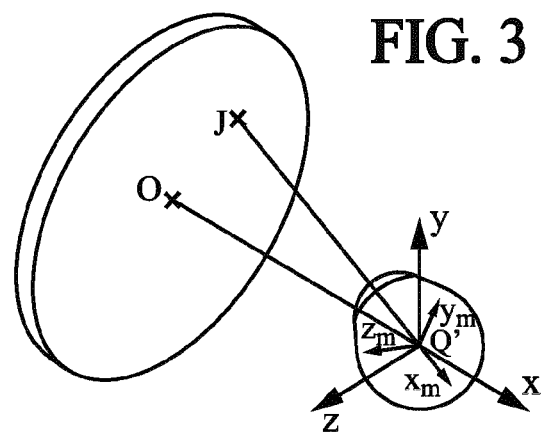
FIG. 3 shows a ray tracing from the center of rotation of the eye.

FIG. 3 represents a perspective view of a configuration wherein the parameters $\alpha$ and $\beta$ are non zero. The effect of rotation of the eye can thus be illustrated by showing a fixed frame $\{x, y, z\}$ and a frame $\{x_m, y_m, z_m\}$ linked to the eye. Frame $\{x, y, z\}$ has its origin at the point Q'. The axis x is the axis Q'O and it is orientated from the lens towards the eye. The y axis is vertical and orientated upwardly. The z axis is such that the frame $\{x, y, z\}$ is orthonormal and direct. The frame $\{x_m, y_m, z_m\}$ is linked to the eye and its center is the point Q'. The $x_m$ axis corresponds to the gaze direction JQ'. Thus, for a primary gaze direction, the two frames $\{x, y, z\}$ and $\{x_m, y_m, z_m\}$ are the same. It is known that the properties for a lens may be expressed in several different ways and notably in surface and optically. A surface characterization is thus equivalent to an optical characterization. In the case of a blank, only a surface characterization may be used. It has to be understood that an optical characterization requires that the lens has been machined to the wearer's prescription. In contrast, in the case of an ophthalmic lens, the characterization may be of a surface or optical kind, both characterizations enabling to describe the same object from two different points of view. Whenever the characterization of the lens is of optical kind, it refers to the ergorama-eye-lens system described above. For simplicity, the term 'lens' is used in the description but it has to be understood as the 'ergorama-eye-lens system'. The value in surface terms can be expressed with relation to points. The points are located with the help of abscissa or ordinate in a frame as defined above with respect to FIGS. 4 and 5.

The values in optic terms can be expressed for gaze directions. Gaze directions are usually given by their degree of lowering and azimuth in a frame whose origin is the center of rotation of the eye. When the lens is mounted in front of the eye, a point called the fitting cross is placed before the pupil or before the eye rotation center Q' of the eye for a primary gaze direction. The primary gaze direction corresponds to the situation where a wearer is looking straight ahead. In the chosen frame, the fitting cross corresponds thus to a lowering angle $\alpha$ of 0° and an azimuth angle $\beta$ of 0° whatever surface of the lens the fitting cross is positioned—rear surface or front surface.

The above description made with reference to FIGS. 1-3 was given for central vision. In peripheral vision, as the gaze direction is fixed, the center of the pupil is considered instead of center of rotation of the eye and peripheral ray directions are considered instead of gaze directions. When peripheral vision is considered, angle $\alpha$ and angle $\beta$ correspond to ray directions instead of gaze directions.

In the remainder of the description, terms like <<up>>, <<bottom>>, <<horizontal>>, <<vertical>>, <<above>>, <<below>>, or other words indicating relative position may be used. These terms are to be understood in the wearing conditions of the lens. Notably, the "upper" part of the lens corresponds to a negative lowering angle $\alpha<0°$ and the "lower" part of the lens corresponds to a positive lowering angle $\alpha>0°$. Similarly, the "upper" part of the surface of a lens—or of a semi-finished lens blank—corresponds to a positive value along the y axis, and preferably to a value along the y axis superior to the y_value at the fitting cross and the "lower" part of the surface of a lens—or of a semi-finished lens blank—corresponds to a negative value along the y axis in the frame as defined above with respect to FIGS. 4 and 5, and preferably to a value along the y axis inferior to the y_value at the fitting cross.

Figure 6:
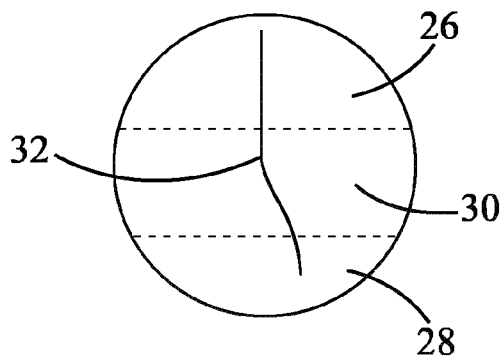
FIGS. 6 and 7 show field vision zones of a lens.
Figure 7:
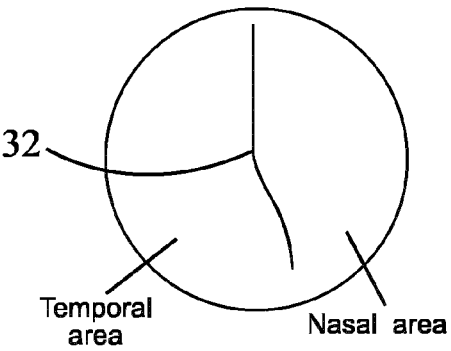

The visual field zones seen through a lens are schematically illustrated in FIGS. 6 and 7. The lens comprises a far vision zone 26 located in the upper part of the lens, a near vision zone 28 located in the lower part of the lens and an intermediate zone 30 situated in the lower part of the lens between the far vision zone 26 and the near vision zone 28. The lens also has a main meridian 32 passing through the three zones and defining a nasal side and a temporal side.

The prescription in ophthalmic field may comprise, in addition to the power prescription, an astigmatism prescription. Such a prescription is composed of an axis value (in degree) and a module value (in diopters). The module value represents the difference between the maximal and minimal power in a given direction allowing to correct the visual default of a wearer. Following the convention, the axis represents the orientation of one of the two powers versus a reference axis and following a given rotation direction. TABO convention may be used. In this convention the reference axis is horizontal and the rotation direction is counterclockwise when looking at the wearer. A 45' axis corresponds to an axis orientated obliquely linking, when looking at the wearer, the upper right quadrant to the lower left quadrant. Such an astigmatism prescription is measured for the wearer in far vision. We use the term 'astigmatism' to refer to the couple (module, axis). That term is sometimes used to designate simply the module. The skilled person easily understands what it refers to depending on the context. The skilled person is also aware that the power/astigmatism prescription for a wearer is commonly described with the terms sphere, cylinder and axis.

So we can define the prescribed far vision mean power value ($P_{FV}$) as the power prescribed plus half of the module of prescribed astigmatism.

The resulting astigmatism is defined as the difference between a prescribed astigmatism and the astigmatism generated by the working lens in the reference frame associated with the eye, and for each direction of glance. Resulting astigmatism may also be called residual astigmatism.

For the purpose of the invention, the meridian line 32 of a progressive lens may be defined as follow: for each lowering of the view of an angle $\alpha=\alpha_1$ between the gaze direction corresponding to the fitting cross and the bottom of the lens, the gaze direction ($\alpha_1$, $\beta_1$) is searched by ray tracing, in order to be able to see clearly the object point located in the median plane, at the distance determined by the ergorama. The median plane is the median plane of the head, preferentially passing through the base of the nose. This plane may also be passing through the middle of right and left eye rotation centers.

Thus, all the gaze directions defined in that way form the meridian line of the ergorama-eye-lens system. For personalization purpose, postural data of the wearer, such as angle and position of the head in the environment, might be taken into account to determine the object position. For instance, the object position might be positioned out of median plane to modelize a wearer lateral shift in near vision.

The meridian line of the lens represents the locus of mean gaze directions of a wearer when he is looking from far to near visions. The meridian line 32 of a surface of the lens is defined as follow: each gaze direction ($\alpha$, $\beta$) belonging to the optical meridian line of the lens intersects the surface in a point (x, y). The meridian line of the surface is the set of points corresponding to the gaze directions of the meridian line of the lens.

As shown in FIG. 7, the meridian 32 separates the lens in a nasal area and a temporal area. As expected, the nasal area is the area of the lens which is between the meridian and the nose of the wearer whereas the temporal area is the area which is between the meridian and the temple of the wearer.

The invention relies on a study by the inventors that right-handed persons and left-handed persons behave differently when performing certain near vision tasks.

The study was conducted on a group of persons who were classified into two categories based on their laterality.

The laterality of a person can be defined by the hand used for writing on a sheet of paper or, more accurately, by calculating a handedness score with the Edinburgh Handedness Inventory which consists in asking a series of questions about the hand used in everyday tasks (Oldfield R. C. (1971), "The assessment and analysis of handedness: The Edinburgh Inventory", Neuropsychologia, vol. 9, p. 97-113).

The specific near vision task of writing on a sheet of paper is then considered.

Figure 8:
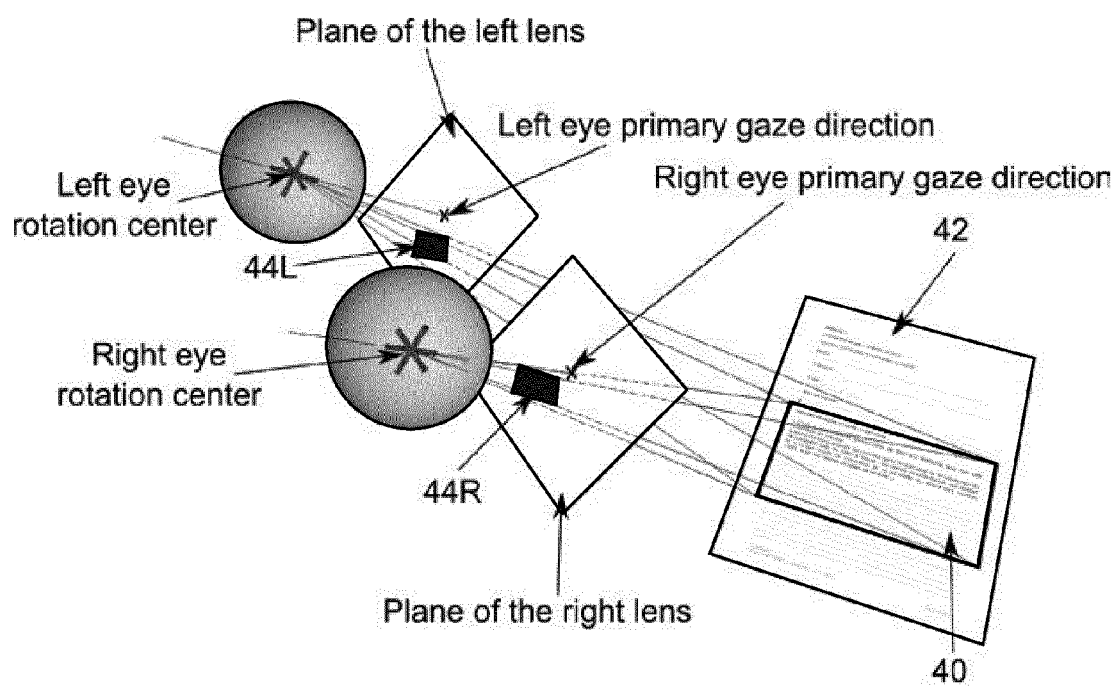
FIG. 8 shows an optical system of eyes and lenses when executing a near vision task.

To this end, as illustrated in FIG. 8, a writing zone 40 of a document 42 is considered and defined as the area of the document 42 where the subject is writing.

Each person of the group is placed in the condition of writing on the writing zone 40.

At this time, the projection 44L, 44R of the writing zone 40 in the plane of the left and the right lens is computed, recorded and analyzed. These projections 44L, 44R are also called useful near vision zones or simply useful zones in the remainder of the description. More generally, useful zones of the lens designate areas of the lens which are intended to be used by the wearer under certain circumstances. This includes useful areas in the parts of the lens for near-vision. Useful zones may vary from one wearer to the other. Further, for a single wearer, useful zones may also vary when taking into account the general context in which the lenses are to be worn, and thus are activity dependent (lenses and hence eyeglasses for shaving, reading, using an e-tablet or a smartphone, writing at the desk, cooking, etc). Useful zones may be determined by eye tracking, for example with tracking glasses.

Figure 9:
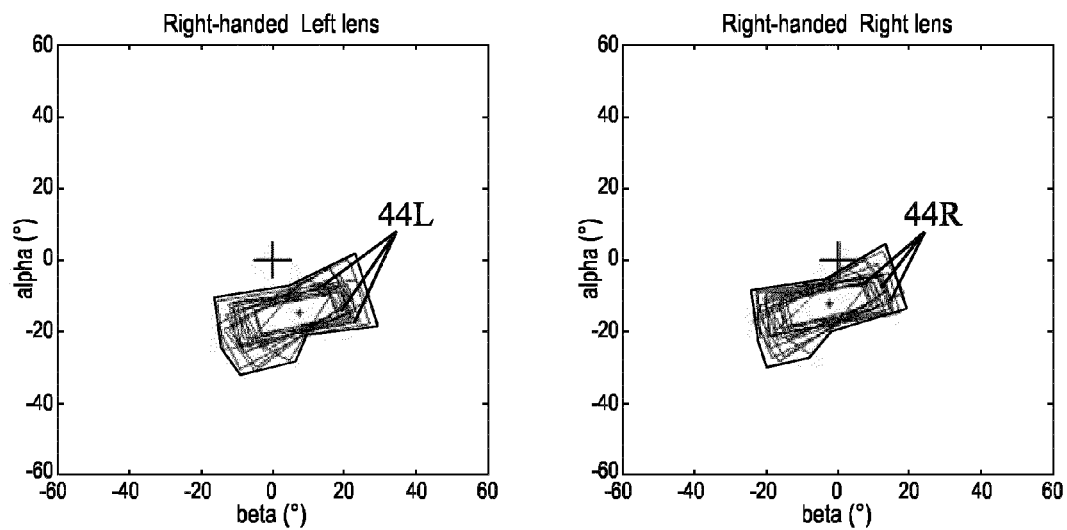
FIGS. 9 and 10 show projections on lens planes of a useful zone when swept by the optical system of FIG. 13.
Figure 10:
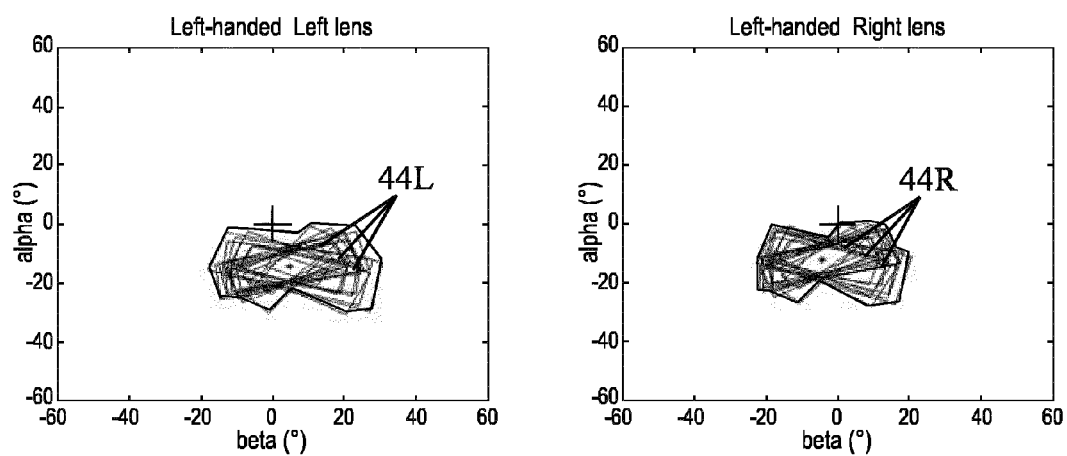

FIG. 9 shows superposition of the useful zones 44L, 44R recorded for right-handed persons who sustained the experience and FIG. 10 shows superposition of the useful zones 44L, 44R for left-handed persons who sustained the experience.

From these FIGS. 9-10, it can be seen that the useful zones 44L, 44R greatly differ between right-handed and left-handed persons, Besides, there is a high variability of the useful zones among left-handed persons, leading to a mean useful zone which is large and substantially aligned along an axis parallel to the horizontal axis ($\alpha=0°$). On the contrary, among right-handed persons, the variability of the useful zones is reduced, leading to a mean useful zone which is smaller and substantially inclined relative to the horizontal axis. Table 1 summarizes the useful zones identified.

The useful zones 44L, 44R can thus be exploited based on their orientation relative to the horizontal axis.

TABLE 1

|  | Left-handed | | Right-handed | |
| --- | --- | --- | --- | --- |
|  | Left lens | Right lens | Left lens | Right lens |
| Minimum angle of inclination (°) | −26 | −28 | 7 | 7 |
| Maximum angle of inclination (°) | 52 | 49 | 54 | 48 |

TABLE 1-continued

|  | Left-handed | | Right-handed | |
| --- | --- | --- | --- | --- |
|  | Left lens | Right lens | Left lens | Right lens |
| Standard deviation (°) | 22 | 22 | 12 | 11 |
| Mean angle of inclination (°) | 7 | 6 | 20 | 19 |

The angle of inclination (θ) can be determined as follows: the wearer is provided with a sheet of paper with printed text. The text consists of a plurality of parallel lines of text. The wearer is requested to settle into a reading position to read the text, and the lines of the text are projected in the system of coordinates for each lens. The system of coordinates for one eye is centered on the center of rotation of the eye and uses (α,β) parameters as described above. See also FIGS. 1-2. The angle of inclination 0 is defined as the angle, in degrees, between the projected line (projection of the text line in the lens plane) and the 'horizontal' line of the lens (line for which α=0 in the (Q', α, β) system of coordinates of the lens.

The angle of inclination (θ) can vary between −90° and 90°. A positive value corresponds to the inclination represented on FIG. 9 for instance.

Based on the data collected and expressed in Table 1, on average, the right-handed persons incline the document 42 by an angle of about 20° when performing a near vision task such as writing, whereas for the left-handed persons, the inclination is not significantly different from 0', so the mean inclination angle is considered to be 0°.

Such a high variability in the orientation of document 42 in writing tasks demonstrates the existence of specific behaviours between right-handed and left-handed persons and therefore implies a need to provide different designs in near vision for right-handed and left-handed wearers. Particularly, the near vision zone of the lenses have to be adapted to match in an optimal way the mean projection on the respective lenses of the useful zone swept during a near vision task.

A first aspect of the invention thus consists in providing two different designs of a pair of progressive ophthalmic lenses, one specific design for left-handed persons and one specific design for right-handed persons.

First, a proximate vision gaze direction ($\alpha_{PV}$, $\beta_{PV}$) is defined for each lens of the pair, that is to say a left proximate vision gaze direction ($\alpha_{PVL}$, $\beta_{PVL}$) for the left-eye lens of the pair and a right proximate vision gaze direction ($\alpha_{PVR}$, $\beta_{PVR}$) for the right-eye lens of the pair.

The right/left proximate vision gaze direction belongs to the right/left meridian line.

Generally, for a progressive lens, the proximate vision gaze direction, and thus $\alpha_{PV}$, is such that the corresponding refractive power is comprised between the prescribed far vision mean power $P_{FV}$ for this lens plus 50% of the addition A prescribed for this lens and the far vision mean power $P_{FV}$ prescribed for this lens plus 125% of the addition prescribed for this lens. Point PV is a proximate vision control point which is defined as the point on the front surface of the lens intersecting the proximate vision gaze direction.

Advantageously, the proximate vision gaze direction, and thus $\alpha_{PV}$, is defined, for each lens of the pair, as the gaze direction where the refracting power reaches the far vision mean power $P_{FV}$ prescribed for this lens plus 85% of the addition A prescribed for this lens or as the gaze direction where the refracting power reaches the far vision mean power $P_{FV}$ prescribed for this lens plus 100% of the addition A prescribed for this lens Second, on each lens of the pair and for each gaze direction (α, β), a refractive power $P_{\alpha,\beta}$ and a module of resulting astigmatism $Asr_{\alpha,\beta}$ are defined.

Then, a left and a right temporal half-width field of refractive power $T_{P\_LE}$, $T_{P\_RE}$ and a left and right nasal half-width field of refractive power $N_{P\_LE}$, $N_{P\_RE}$ are defined respectively for the left-eye lens and the right-eye lens.

For a lens, a temporal half-width field of refractive power $T_P$ is defined as the angular distance, at constant lowering angle α, between the proximate vision gaze direction ($\alpha_{PV}$, $\beta_{PV}$) and a gaze direction ($\alpha_{PV}$, $\beta_{TP}$) on the temporal side of the lens where the refractive power $P_{\alpha PV,\beta TP}$ reaches the value of the prescribed far vision mean power $P_{FV}$ for the lens plus three quarters of the prescribed addition A for the lens:

$$P_{\alpha PV, \beta TP} = P_{FV} + \tfrac{3}{4} * A$$

For a lens, a nasal half-width field of refractive power $N_P$ is defined as the angular distance, at constant lowering angle α, between the proximate vision gaze direction ($\alpha_{PV}$, $\beta_{PV}$) and a gaze direction ($\alpha_{PV}$, $\beta_{PV}$) on the nasal side of the lens where the refractive power $P_{\alpha PV,\beta NP}$ reaches the value of the prescribed far vision mean power $P_{FV}$ for the lens plus three quarters of the prescribed addition A for the lens:

$$P_{\alpha PV, \beta NP} = P_{FV} + \tfrac{1}{4} * A$$

There is further defined a left and a right temporal half-width field of module of resulting astigmatism $T_{A\_LE}$, $T_{A\_RE}$ and a left and right nasal half-width field of refractive power $N_{A\_LE}$, $N_{A\_RE}$ respectively for the left-eye lens and the right-eye lens.

For a lens, a temporal half-width field of module of resulting astigmatism $T_A$ is defined as the angular distance, at constant lowering angle α, between the proximate vision gaze direction ($\alpha_{PV}$, $\beta_{PV}$) and a gaze direction ($\alpha_{PV}$, $\beta_{TA}$) on the temporal side of the lens where the module of resulting astigmatism $Asr_{\alpha PV,\beta TA}$ reaches the value of one quarter of the prescribed addition A for the lens:

$$Asr_{\alpha PV, \beta TA} = A/4$$

For a lens, a nasal half-width field of module of resulting astigmatism $N_A$ is defined as the angular distance, at constant lowering angle α, between the proximate vision gaze direction ($\alpha_{PV}$, $\beta_{PV}$) and a gaze direction ($\alpha_{PV}$, $\beta_{NA}$) on the nasal side of the lens where the module of resulting astigmatism $Asr_{\alpha PV,\beta NA}$ reaches the value of one quarter of the prescribed addition A for the lens:

$$Asr_{\alpha PV, \beta NA} = A/4$$

The criteria taken into account in the following are the ratio $R_{PL}$, $R_{PR}$ of the difference over the sum of temporal and nasal half-width fields of refractive power for the left-eye lens and the right-eye lens, and the ratio $R_{AL}$, $R_{AR}$ of the difference over the sum of temporal and nasal half-width fields of module of resulting astigmatism for the left-eye lens and the right-eye lens:

$$R_{PL} = \frac{T_{P\_LE} - N_{P\_LE}}{T_{P\_LE} + N_{P\_LE}}$$

$$R_{PR} = \frac{T_{P\_RE} - N_{P\_RE}}{T_{P\_RE} + N_{P\_RE}}$$

$$R_{AL} = \frac{T_{A\_LE} - N_{A\_LE}}{T_{A\_LE} + N_{A\_LE}}$$

-continued $$R_{AR} = \frac{T_{A\_RE} - N_{A\_RE}}{T_{A-RE} + N_{A\_RE}}$$

For each lens of the pair, at least one criterion is determined based on the laterality of the wearer, that is to say either the ratio of refractive power $R_P$ or the ratio of module of resulting astigmatism $R_A$ or both.

According to the results summarized in Table 1 above and explained with reference to FIGS. 9 and 10, the chosen criterion is determined differently for the left-handed and right-handed persons.

For the left-handed persons, as the inclination relative to the horizontal axis of the projections of the writing zone 40 on the plane of the left-eye and right-eye lenses is substantially equal to 0°, the design for both the left-eye and right-eye lenses is symmetric relative to the corresponding proximate vision gaze direction ($\alpha_{PVL}$, $\beta_{PVL}$), ($\alpha_{PVR}$, $\beta_{PVR}$).

This condition is expressed by the fact that, for the left-handed persons, the ratio of the difference over the sum of temporal and nasal half-width fields of refractive power is set substantially to 0 for each lens of the pair and/or the ratio of the difference over the sum of temporal and nasal half-width fields of module of resulting astigmatism is set substantially to 0 for each lens of the pair:

$R_{PL}=R_{PR}=0$ and/or $R_{AL}=R_{AR}=0$

These equations result in the fact that, for the left-handed persons, the left and right temporal half-width fields of refractive power are substantially equal respectively to the left and right nasal half-width fields of refractive power and/or the left and right temporal half-width fields of module of resulting astigmatism are substantially equal respectively to the left and right nasal half-width fields of module of resulting astigmatism:

$T_{P\_LE}=N_{P\_LE}$ and $T_{P\_RE}=N_{P\_RE}$ and/or $T_{A\_LE}=N_{A\_LE}$ and $T_{A\_RE}=N_{A\_RE}$ Table 2 summarizes the values of the criteria of resulting astigmatism $R_{AL}$, $R_{AR}$ for the left-handed persons, for a proximate vision gaze direction where the refractive power reaches $P_{FV}$ plus 85% of the prescribed addition and for a proximate vision gaze direction where the refractive power reaches $P_{FV}$ plus 100% of the prescribed addition.

TABLE 2

|  | Left-handed criteria | |
| --- | --- | --- |
|  | $P_{\alpha PV, \beta PV}=$ $P_{FV}+85\% * A$ | $P_{\alpha PV, \beta PV}=$ $P_{FV}+100\% * A$ |
| Mean value | 0.00 | 0.00 |
| Tolerance range | ±0.12 | ±0.12 |
| Preferred value | 0.00 | 0.00 |

In another embodiment, more generally, for a left-handed wearer, the ratio of the difference over the sum of temporal and nasal half-width fields of refractive power is set to a value less than or equal substantially to 0 for the right-eye lens (($T_{P\_RE}-N_{P\_RE}$)/($T_{P\_RE}+N_{P\_RE}$)≤0) and/or the ratio of the difference over the sum of temporal and nasal half-width fields of module of resulting astigmatism is set to a value less than or equal substantially to 0 for the right-eye lens (($T_{A\_RE}-N_{A\_RE}$)/($T_{A\_RE}+N_{A\_RE}$)≤0), and the ratio of the difference over the sum of temporal and nasal half-width fields of refractive power is set to a value greater than or equal substantially to 0 for the left-eye lens (($T_{P\_LE}-N_{P\_LE}$)/($T_{P\_LE}+N_{P\_LE}$)≥0) and/or the ratio of the difference over the sum of temporal and nasal half-width fields of module of resulting astigmatism is set to a value greater than or equal substantially to 0 for the left-eye lens (($T_{A\_LE}-N_{A\_LE}$)/($T_{A\_LE}+N_{A\_LE}$)≥0).

For a left handed wearer:

$R_{PR}\leq0$ and $R_{PL}\geq0$ and/or $R_{AR}\leq0$ and $R_{AL}\geq0$ or $R_{PR}<0$ and $R_{PL}>0$ and/or $R_{AR}<0$ and $R_{AL}>0$ In all embodiments described therein, where a given ratio is set to a value less than or equal substantially to zero, said ratio may be set to a value <0. Similarly, for all embodiments, where a given ratio is set to a value greater than or equal substantially to zero, said ratio may be set to a value >0.

For the right-handed persons, as the projections of the writing zone 40 on the plane of the left-eye and right-eye lenses is inclined by an angle of about 20° relative to the horizontal axis, the design for both the left-eye and right-eye lenses is dissymmetric relative to the corresponding proximate vision gaze direction ($\alpha_{PVL}$, $\beta_{PVL}$), ($\alpha_{PVR}$, $\beta_{PVR}$).

This condition is expressed by the fact that, for the right-handed persons, the ratio of the difference over the sum of temporal and nasal half-width fields of refractive power is set to a value greater than or equal substantially to 0 for the right-eye lens and the ratio of the difference over the sum of temporal and nasal half-width fields of refractive power is set to a value less than or equal substantially to 0 for the left-eye lens and/or the ratio of the difference over the sum of temporal and nasal half-width fields of module of resulting astigmatism is set to a value greater than or equal substantially to 0 for the right-eye lens and the ratio of the difference over the sum of temporal and nasal half-width fields of module of resulting astigmatism is set to a value less than or equal substantially to 0 for the left-eye lens:

$R_{PR}\geq0$ and $R_{PL}\leq0$ and/or $R_{AR}\geq0$ and $R_{AL}<0$

These equations result in the fact that, for the right-handed persons, the right temporal half-width field of refractive power is greater than or equal substantially to the right nasal half-width field of refractive power and the left temporal half-width field of refractive power is less than or equal substantially to the left nasal half-width field of refractive power and/or the right temporal half-width field of module of resulting astigmatism is greater than or equal substantially to the right nasal half-width field of module of resulting astigmatism and the left temporal half-width field of module of resulting astigmatism is less than or equal substantially to the left nasal half-width field of module of resulting astigmatism:

$T_{P\_RE}\geq N_{P\_RE}$ and $T_{P\_LE}\leq N_{P\_LE}$ and/or $T_{A\_RE}\geq N_{A\_RE}$ and $T_{A\_LE}\leq N_{A\_LE}$ In particular, for the right-handed persons, the sum of the ratio of the difference over the sum of temporal and nasal half-width fields of refractive power for the right-eye lens and the ratio of the difference over the sum of temporal and nasal half-width fields of refractive power for the left-eye lens is set substantially to 0 and/or the sum of the ratio of the difference over the sum of temporal and nasal half-width fields of module of resulting astigmatism for the right-eye lens and the ratio of the difference over the sum of temporal and nasal half-width fields of module of resulting astigmatism for the left-eye lens is set substantially to 0:

$$R_{PR}+R_{PL}=0$$

and/or $$R_{AR}+R_{AL}=0$$

Table 3 summarizes the values of the criteria of resulting astigmatism $R_{AL}$, $R_{AR}$ for the right-handed persons, for a proximate vision gaze direction where the refractive power reaches $P_{FV}$ plus 85% of the prescribed addition and for a proximate vision gaze direction where the refractive power reaches $P_{FV}$ plus 100% of the prescribed addition.

TABLE 3

| | Right-handed criteria | |
|---|---|---|
| | $P_{\alpha PV, \beta PV} =$ $P_{FV} + 85\% * A$ | $P_{\alpha PV, \beta PV} =$ $P_{FV} + 100\% * A$ |
| Right-eye lens values | >0.12 | >0.12 |
| Preferred right-eye lens value | 0.15 | 0.20 |
| Left-eye lens values | <−0.12 | <−0.12 |
| Preferred left-eye lens value | −0.15 | −0.20 |

Further, in addition to the above feature, the invention provides a pair of lenses intended for a right-handed wearer, wherein for respectively each lens of the pair, $\Delta \leq 10\%$, with $\Delta = 100*$abs(Max_Asr_N−Max_Asr_T)/Max(Max_Asr_N; Max_Asr_T), abs: absolute value, Max_Asr_N: maximum value of resulting astigmatism found over an area of the lens defined by all gaze directions which are comprised:
  within the nasal area of the lens, and
  within a zone centered on the gaze direction passing through the PRP (Prism reference point) and containing all gaze directions ($\alpha,\beta$) respecting the following inequality $(\alpha^2+\beta^2)^{1/2} \leq 40°$, Max_Asr_T: maximum value of resulting astigmatism found over an area of the lens defined by all gaze directions which are comprised:
  within the temporal area of the lens, and
  within a zone centered on the gaze direction passing through the PRP (Prism reference point) and containing all gaze directions ($\alpha,\beta$) respecting the following inequality $(\alpha^2+\beta^2)^{1/2} \leq 40°$, Max(x;y): whichever value of x and y is higher.

The nasal and temporal sides of the lens are determined with respect to the meridian line of the lens.

Advantageously according to the invention, $\Delta \leq 10\%$, and preferably $\Delta \leq 8\%$, more preferably $\Delta \leq 5\%$. This feature sets a maximum value for the relative imbalance of resulting astigmatism between the nasal and temporal sides of each lens. Correspondingly, even though the values for nasal and temporal half-width fields are asymmetric on a given lens for near (proximate) vision to reflect laterality, this asymmetry is counterbalanced by a relative (controlled) general symmetry of the lens design in terms of peak values of resulting astigmatism. This is particularly advantageous for lens performance in a situation of dynamic vision and/or peripheral vision.

Therefore, the invention provides two specific designs for a pair of progressive ophthalmic lenses according to the laterality of the wearer.

According to another aspect, the invention provides a process for determining a pair of personalized progressive ophthalmic lenses intended for a particular wearer.

This process differs from the above process relating to a left-handed/right-handed segmentation in that the useful near vision zones 44L, 44R of this wearer and the inclination of the useful near vision zones 44L, 44R are measured and the criteria are determined based on the measured inclination.

Consequently, the obtained design is adapted to this particular wearer and not to the average of the left-handed or right-handed persons.

Obviously, other near vision tasks such as reading, writing on a computer, using a smartphone, etc could be considered.

In the processes of the invention, the design can be further refined by taking into account a head/eye behaviour of the wearer.

Indeed, when executing a near vision task, some persons rather tend to move their eyes and other persons rather tend to move their head.

The inventors have found that, for a eye mover wearer, the areas of the lenses actually used correspond to the full projections on the lenses of the writing zone 40, whereas for a head mover wearer, the areas of the lenses actually used correspond to a fraction of the projections on the lenses of the writing zone 40.

A head/eye behaviour score can be calculated and the projection of the writing zone 40 can be weighted by a coefficient which depends on the head/eye behaviour score. The head/eye behaviour score can be measured using an apparatus known under the name Visioffice or Vision Print System, or the head/eye behaviour score can be determined by eye tracking, such as SMI Eye tracking glasses (SensoMotoric Instrument), ASL eye tracking glasses (Applied Science Laboratories), etc.

According to one embodiment, head/eye behaviour can be assessed as follows. The wearer is placed opposite a strip with three off-centre lights at −40°, 0°, +40° and a wearer/target distance of 40 cm. An audible signal sounds and the central light is turned on for a random duration (between 1.5 s and 2.5 s) corresponding to staring straight forward. When it is turned off one of the two peripheral lights is turned on (1 s). The instruction given to the wearer is to continually stare at the light turned on. Measurement of the distance to the target and the angle of rotation of the head is performed using a tracking system such as a Polhemus Fastrak system (6 axis measurement system without contact). The patient is presented with about twenty central light/peripheral light cycles, balanced between right and left. The choice as to which side will be stimulated is made at random with, however, no more than two successive presentations on the same side. In order to qualify the wearer's propensity to move the head more or less, one can use a variable known as Gain or head/eye coefficient which gives the proportion of head movements in the total movements useful to reach the target. It is expressed as: Gain=(head angle)/(target angle). The average angle is calculated separately to the right and to the left. The value taken for the measurement corresponds to the gain associated with the lowest typical difference. In this measurement method, a 'full eye mover' has a gain of 0.00 and a 'full head mover' has a gain of 1.00.

One of skill in the art appreciates that the method may be modified or adapted with variants (for example variants for the position of the lights, for duration of the sounds or of the light signals, for the number of cycles, etc.), and that notably a Reverse Gain may be calculated to describe a head/eye behaviour:

(Reverse gain)=[1−Gain]=[1−(head angle)/(target angle)].

Impact of head/eye behaviour on lens design is known in the art, as for example from WO 2006/072683.

The invention shall be further illustrated by the following examples.

GENERAL DESCRIPTION OF THE FIGURES OF THE EXAMPLES

FIGS. 11 to 22 give optical characteristics of the lenses considered.

FIGS. 11, 13, 15, 17, 19 and 21 are refractive power maps. The vertical and horizontal axes of the maps are the values of the lowering angle $\alpha$ and azimuth angle $\beta$ of the gaze directions. The isometric curves indicated on these maps connect gaze directions which correspond to a same refractive power value. The respective refractive power values for the curves are incremented by $0.25\delta$ between neighbouring curves, and are indicated on some of these curves.

FIGS. 12, 14, 16, 18, 20 and 22 are resulting astigmatism maps. The axes of these maps are similar to those of the refractive power maps and the isometric curves indicated on these maps connect gaze directions which correspond to a same resulting astigmatism value.

On each of these maps, three specific points PV, A and B are considered.

Point PV is a proximate vision control point which is defined as the point on the front surface of the lens intersecting the proximate vision gaze direction.

In the examples below, point PV is the point on the front surface of the lens intersecting the gaze direction where the refractive power reaches the far vision mean power prescribed for that lens plus 100% of the addition prescribed for that lens.

Point A is located on the temporal side of the lens such that the distance between point A and point PV corresponds to the temporal half-width field as defined above.

Point B is located on the nasal side of the lens such that the distance between point B and point PV corresponds to the nasal half-width field as defined above.

Example 1

FIGS. 11 to 14

Example 1 corresponds to a pair PAIR1 of progressive ophthalmic lenses according to the invention intended for a right-handed wearer and which has been optimized in terms of resulting astigmatism.

In this case, the power prescription is $+0.75\delta$ in far vision and the prescribed addition is $1.50\delta$ for both lenses of the pair. No astigmatism is prescribed for the wearer.

Figure 11:
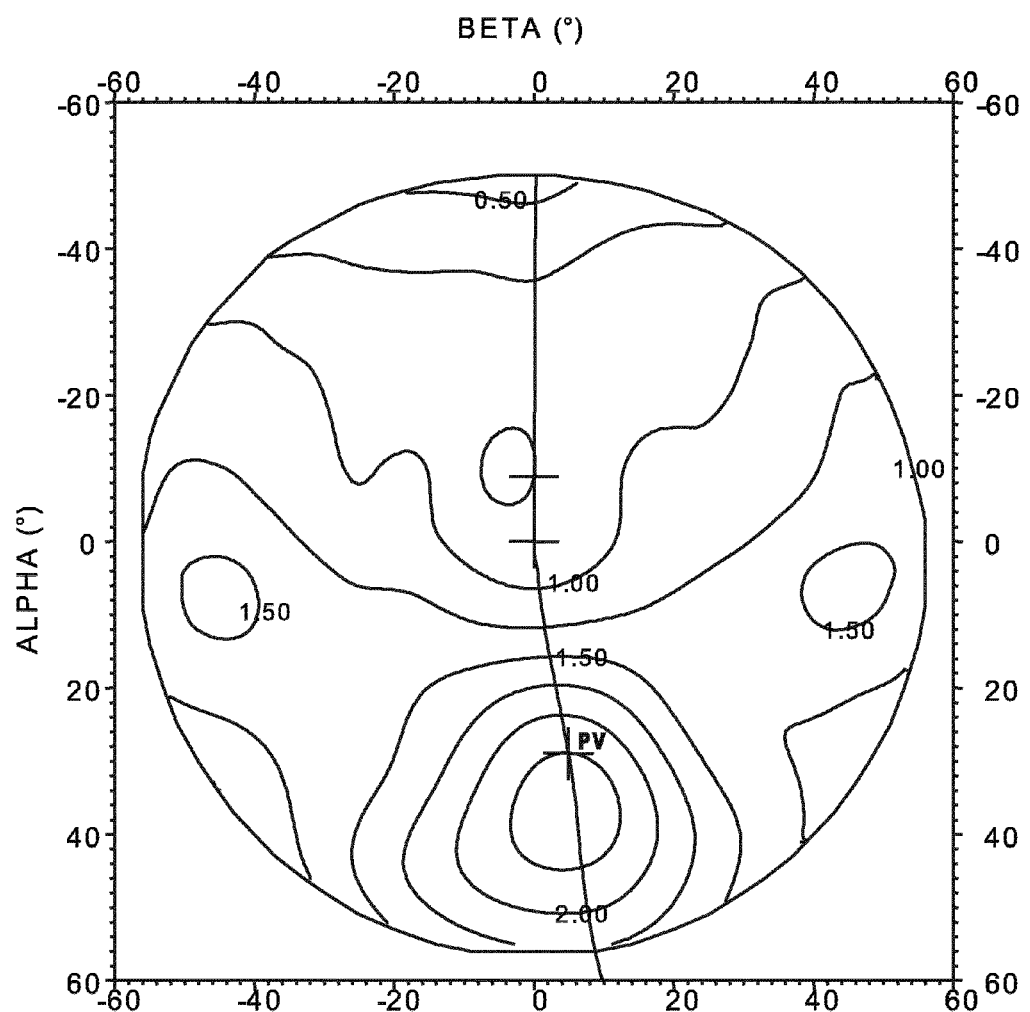
FIGS. 11 to 22 give optical characteristics for three examples of pair of progressive ophthalmic lenses according to the invention.
Figure 12:
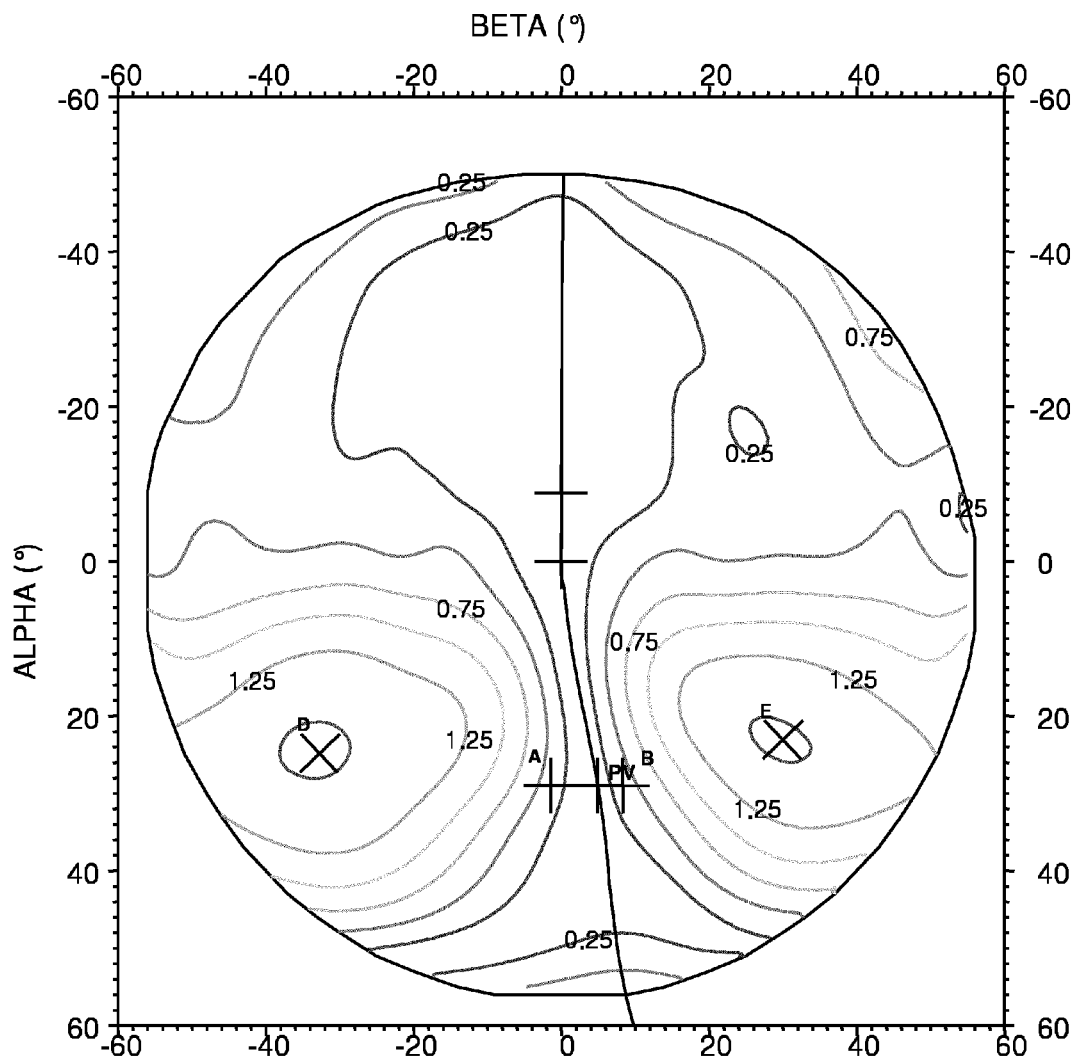

FIGS. 11 and 12 give optical characteristics (refractive power and resulting astigmatism) of the right-eye lens LENS1 of the pair.

Figure 13:
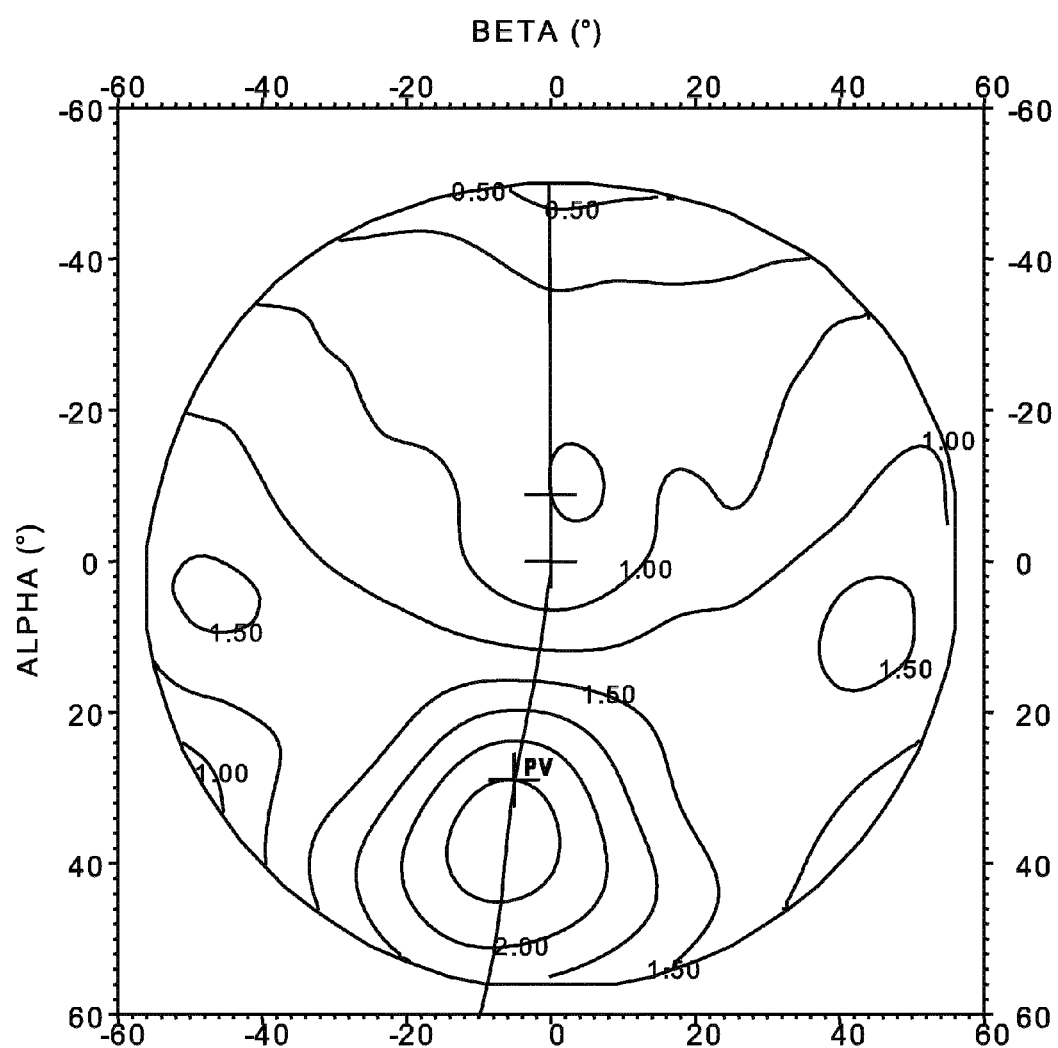
Figure 14:
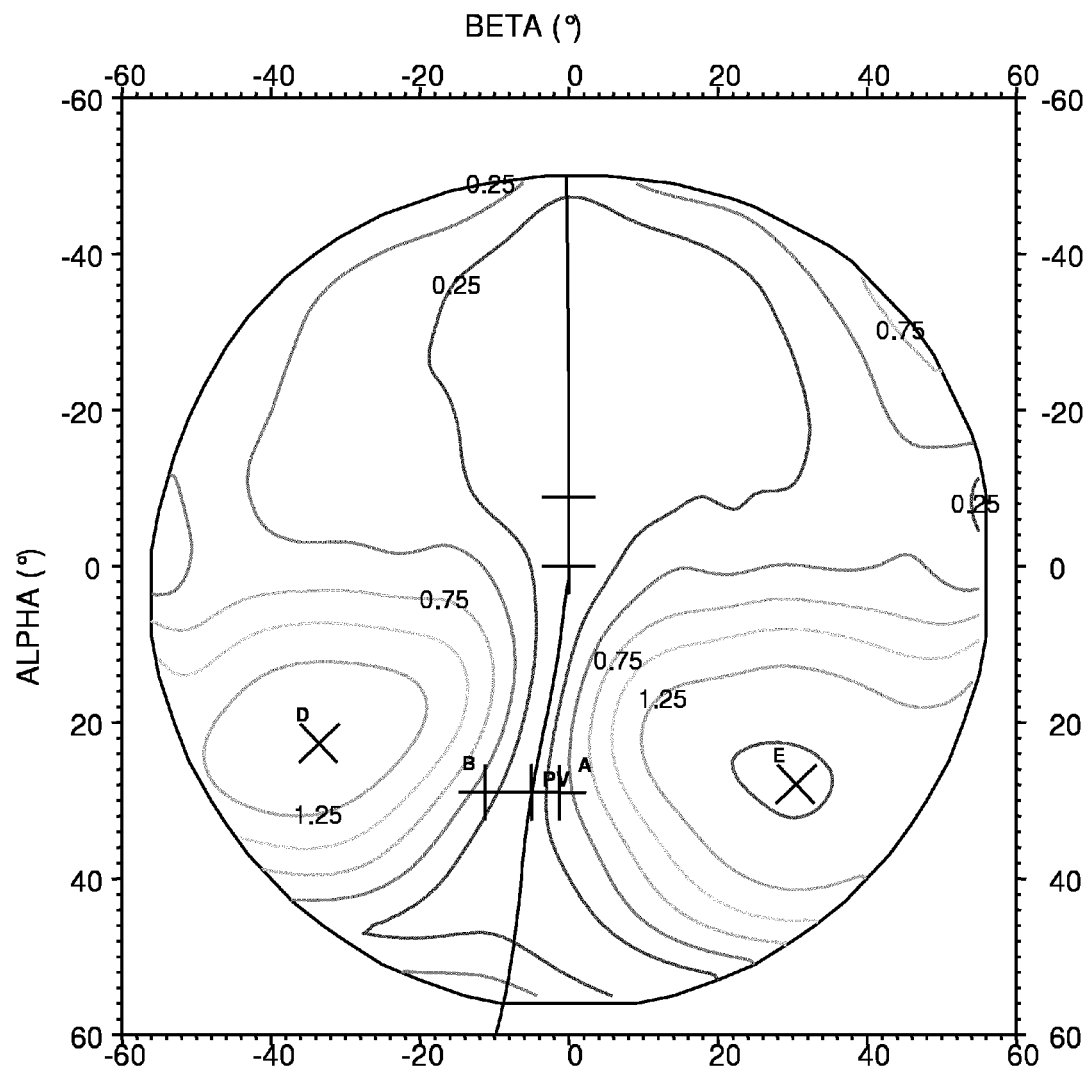

FIGS. 13 and 14 give optical characteristics (refractive power and resulting astigmatism) of the left-eye lens LENS2 of the pair.

On FIG. 11:
Point PV is located at $\alpha_{PVR}=28.9°$ and $\beta_{PVR}=4.9°$
Point PV is located on the isometric curve corresponding to a power value:

$P=0.75+100\%*1.5=2.25\delta$

On FIG. 12:
point PV is located at $\alpha_{PVR}=28.9°$ and $\beta_{PVR}=4.9°$
point A is located at $\alpha_{AR}=\alpha_{AR}=28.9°$ and $\beta_{AR}=-1.4°$
point B is located at $\alpha_{BR}=\alpha_{BR}=28.9°$ and $\beta_{BR}=8.4°$
The isometric curve connecting points A and B correspond to a resulting astigmatism value:

$Asr\ 1.5/4=0.375\delta$ $T_{A\_RE}=6.3'$ and $N_{A\_RE}=3.5°$

Then $R_{AR}=0.28$
On FIG. 13:
Point PV is located at $\alpha_{PVL}=29.0°$ and $\beta_{PVL}=-4.9°$
Point PV is located on the isometric curve corresponding to a power value:

$P=0.75+100\%*1.5=2.25\delta$

On FIG. 14:
point PV is located at $\alpha_{PVL}=29.0°$ and $\beta_{PVL}=-4.9°$
point A is located at $\alpha_{AI}=\alpha_{PVL}=29.0°$ and $\beta_{AL}=-1.2°$
point B is located at $\alpha_{BL}=\alpha_{PVL}=29.0°$ and $\beta_{BL}=-11.3°$
The isometric curve connecting points A and B correspond to a resulting astigmatism value:

$Asr=1.5/4=0.375\delta$ $T_{A\_LE}=3.7°$ and $N_{A\_LE}=6.4°$

Then $R_{AL}=-0.27$
This pair PAIR1 is intended for a right-handed person. Indeed, the resulting astigmatism ratios are such that:

$R_{AR}\geq 0$ and $R_{AL}\leq 0$

The ratios are further such that $R_{AR}+R_{AL}$ equals substantially to 0 taking into account the tolerance range ($R_{AR}+R_{AL}=0.01$).

Further, regarding the resulting astigmatism peaks:
For the right eye (FIG. 12):
Max_Asr_T=$1.51\delta$, marked as point D located at:

$\beta\_Max\_Asr\_T=-33'$ $\alpha\_Max\_Asr\_T=25'$

Max_Asr_N=$1.51\delta$, marked as point E located at $\beta\_Max\_Asr\_N=30°$ $\alpha\_Max\_Asr\_N=23°$ in that case, $\Delta=0.0\%$
For the left eye (FIG. 14):
Max_Asr_T=$1.51\delta$, marked as point E located at $\beta\_Max\_Asr\_T=32°$ $\alpha\_Max\_Asr\_T=26°$ Max_Asr_N=$1.49\delta$, marked as point D located at:

$\beta\_Max\_Asr\_N=-33°$ $\alpha\_Max\_Asr\_N=23°$ in that case, $\Delta=1.3\%$.

The pair of lenses of example 1 thus provides optimal comfort to a right-handed wearer by providing a dissymmetric design in useful zones when the wearer performs near vision tasks.

Example 2

FIGS. 15 to 18

Example 2 corresponds to a pair PAIR2 of progressive ophthalmic lenses according to the invention intended for a left-handed wearer and which has been optimized in terms of resulting astigmatism.

In this case, the power prescription is +0.75δ in far vision and the prescribed addition is 1.50δ for both lenses of the pair. No astigmatism is prescribed for the wearer.

Figure 15:
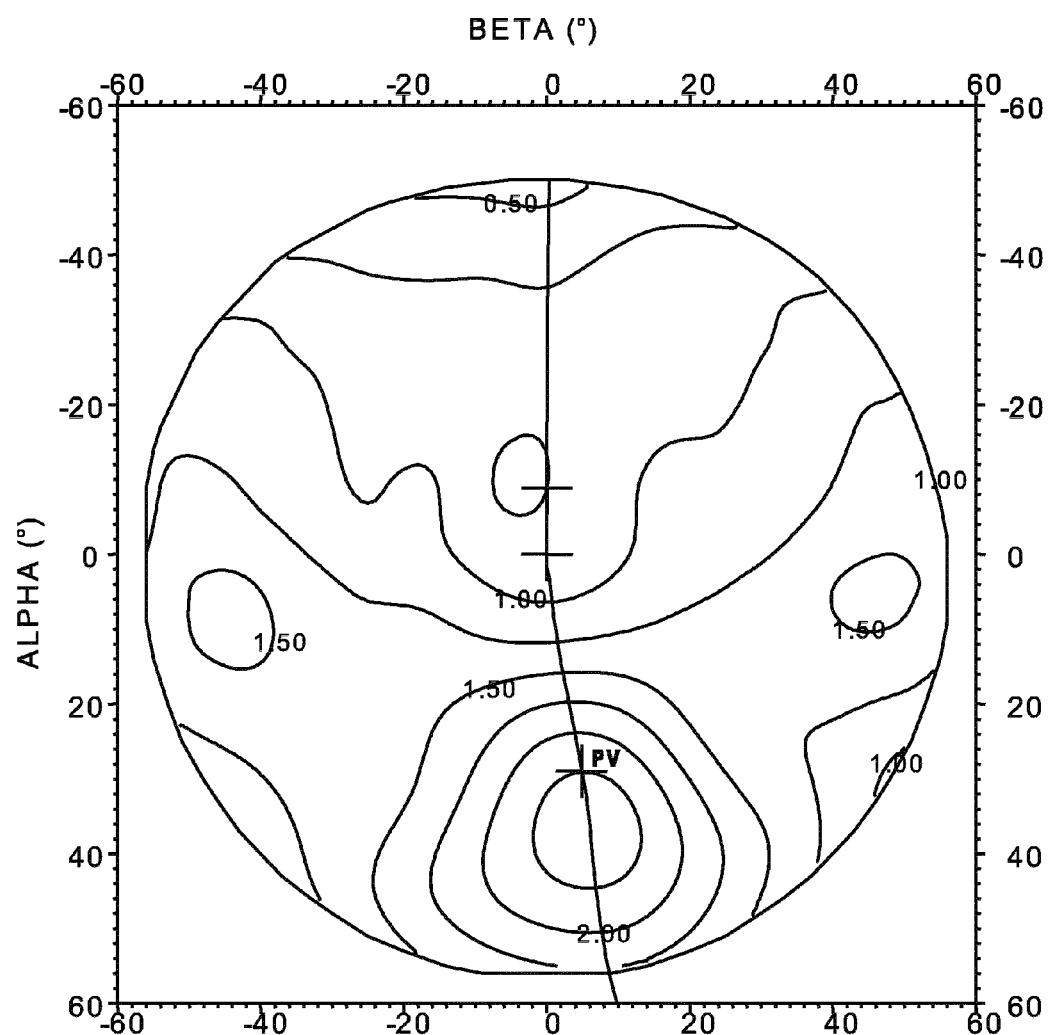
Figure 16:
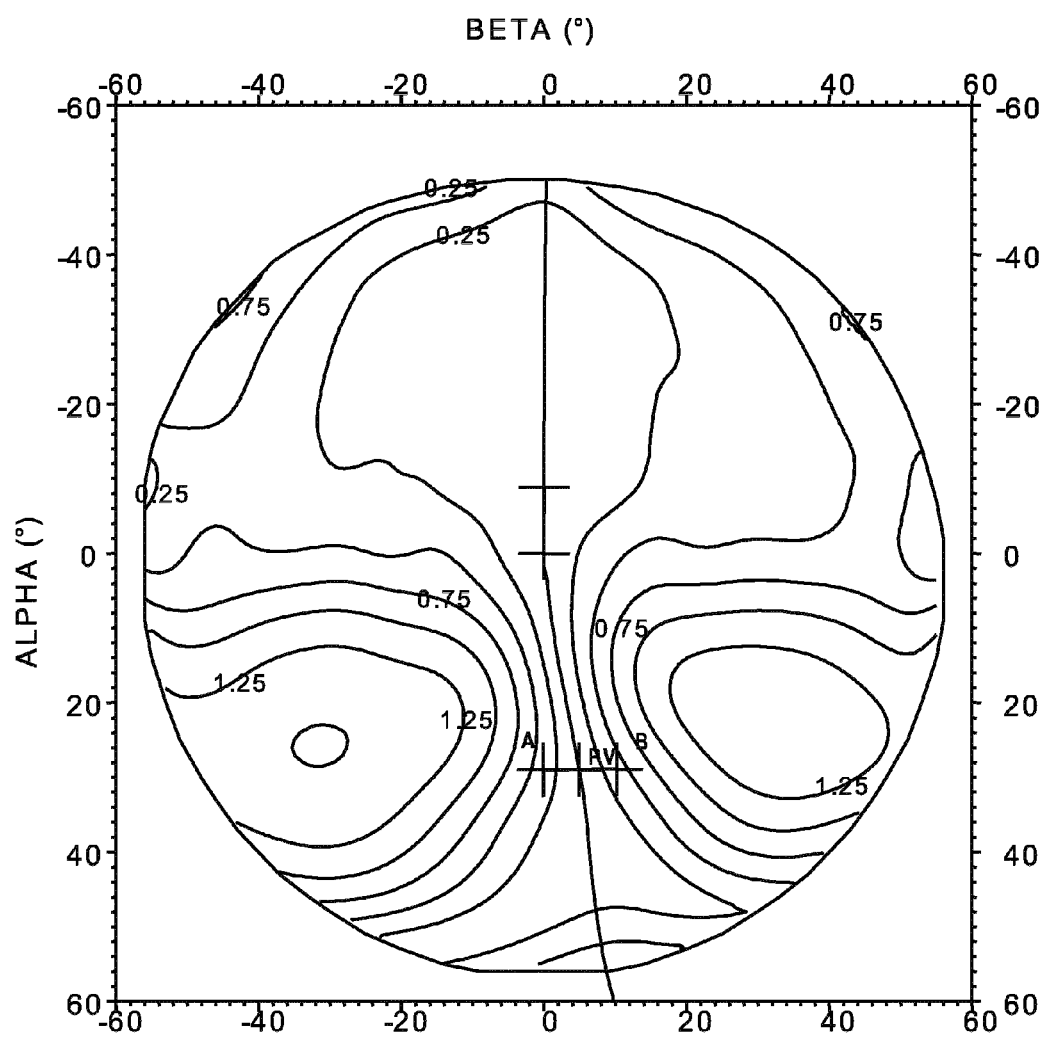

FIGS. 15 and 16 give optical characteristics (refractive power and module of resulting astigmatism) of the right-eye lens LENS3 of the pair.

Figure 17:
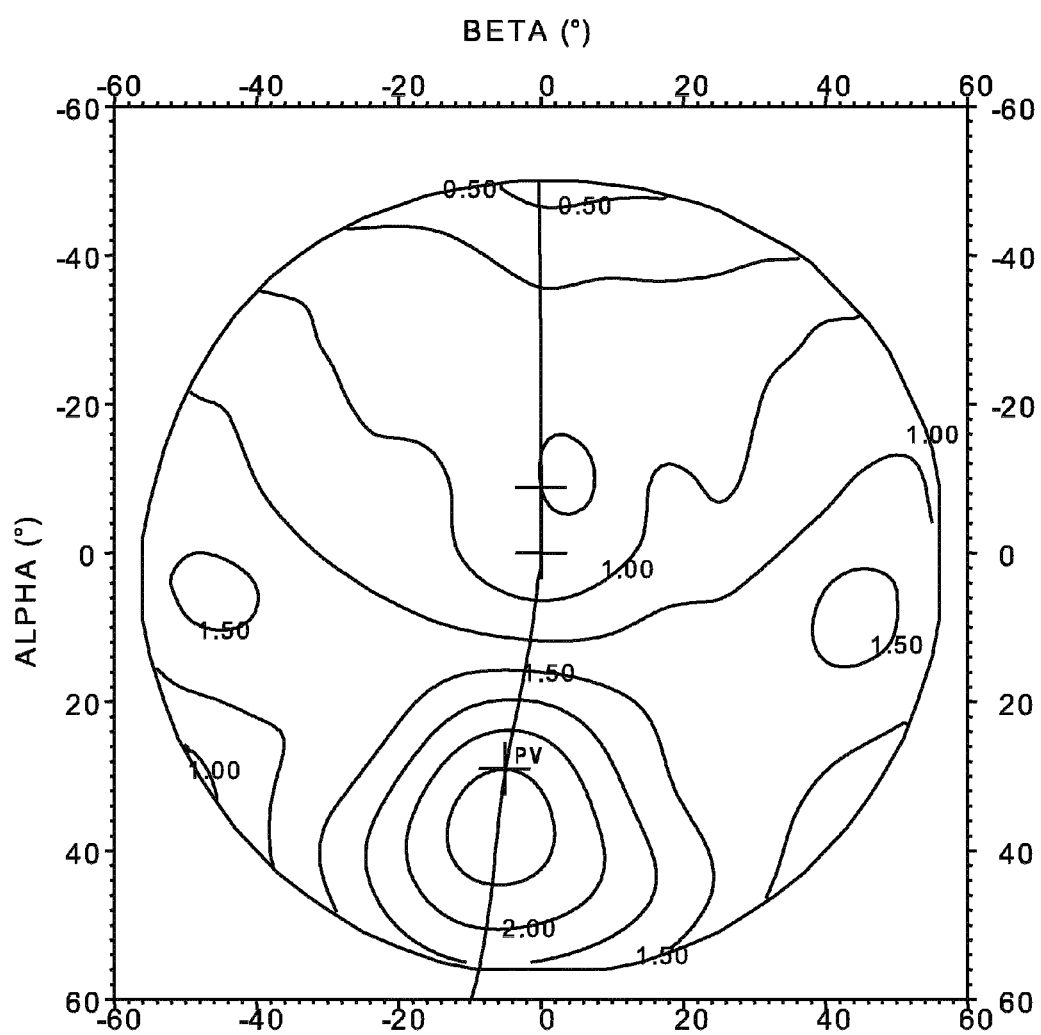
Figure 18:
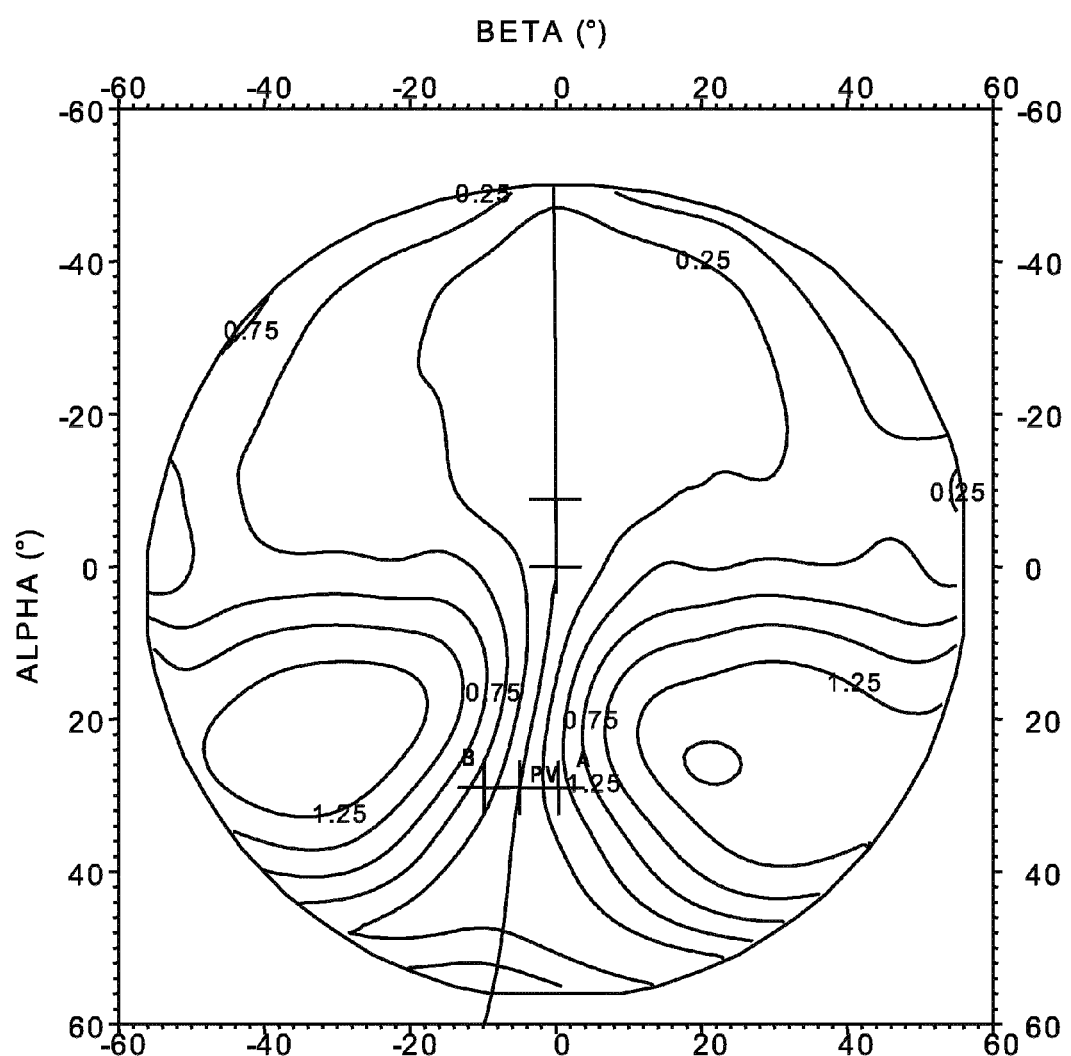

FIGS. 17 and 18 give optical characteristics (refractive power and module of resulting astigmatism) of the left-eye lens LENS4 of the pair.

On FIG. 15:

Point PV is located at $\alpha_{PVR}=29.1°$ and $\beta_{PVR}=5.0°$

Point PV is located on the isometric curve corresponding to a power value:

$P=0.75+100\%*1.5=2.25\delta$

On FIG. 16:

point PV is located at $\alpha_{PVR}=29.1°$ and $\beta_{PVR}=5.0°$
point A is located at $\alpha_{AR}=\alpha_{PVR}=29.1'$ and $\beta_{AR}=-0.1°$
point B is located at $\alpha_{BR}=\alpha_{PVR}=29.1'$ and $\beta_{BR}=10.1°$ The isometric curve connecting points A and B correspond to a resulting astigmatism value:

$Asr=1.5/4=0.375\delta$ $T_{A\_RE}=5.1°$ and $N_{A\_RE}=5.1°$

Then $R_{AR}=0.00$

On FIG. 17:

Point PV is located at $\alpha_{PVL}=29.1°$ and $P_{PVL}=-5.0°$

Point PV is located on the isometric curve corresponding to a power value:

$P=0.75+100\%*1.5=2.25\delta$

On FIG. 18:

point PV is located at $\alpha_{PVL}=29.1°$ and $\beta_{PVL}=-5.0°$
point A is located at $\alpha_{AI}=\alpha_{PVL}=29.1°$ and $\beta_{AL}=0.1°$
point B is located at $\alpha_{BL}=\alpha_{PVL}=29.1°$ and $\beta_{BL}=-10.1°$ The isometric curve connecting points A and B correspond to a resulting astigmatism value:

$Asr=1.5/4=0.375\delta$ $T_{A\_LE}=5.1°$ and $N_{A\_LE}=5.1°$

Then $R_{AL}=0.00$

This pair PAIR2 is intended for a left-handed person. Indeed, the resulting astigmatism ratios are such that:

$R_{AL}=R_{AR}=0$

The pair of lenses of example 2 thus provides optimal comfort to a left-handed wearer by providing a symmetric design in useful zones when the wearer performs near vision tasks.

Example 3

FIGS. 19 to 22

Example 3 corresponds to a pair PAIR3 of progressive ophthalmic lenses according to the invention intended for a left-handed wearer and which has been optimized in terms of resulting astigmatism.

In this case, the power prescription is +0.75δ in far vision and the prescribed addition is 1.50δ for both lenses of the pair. No astigmatism is prescribed for the wearer.

Figure 19:
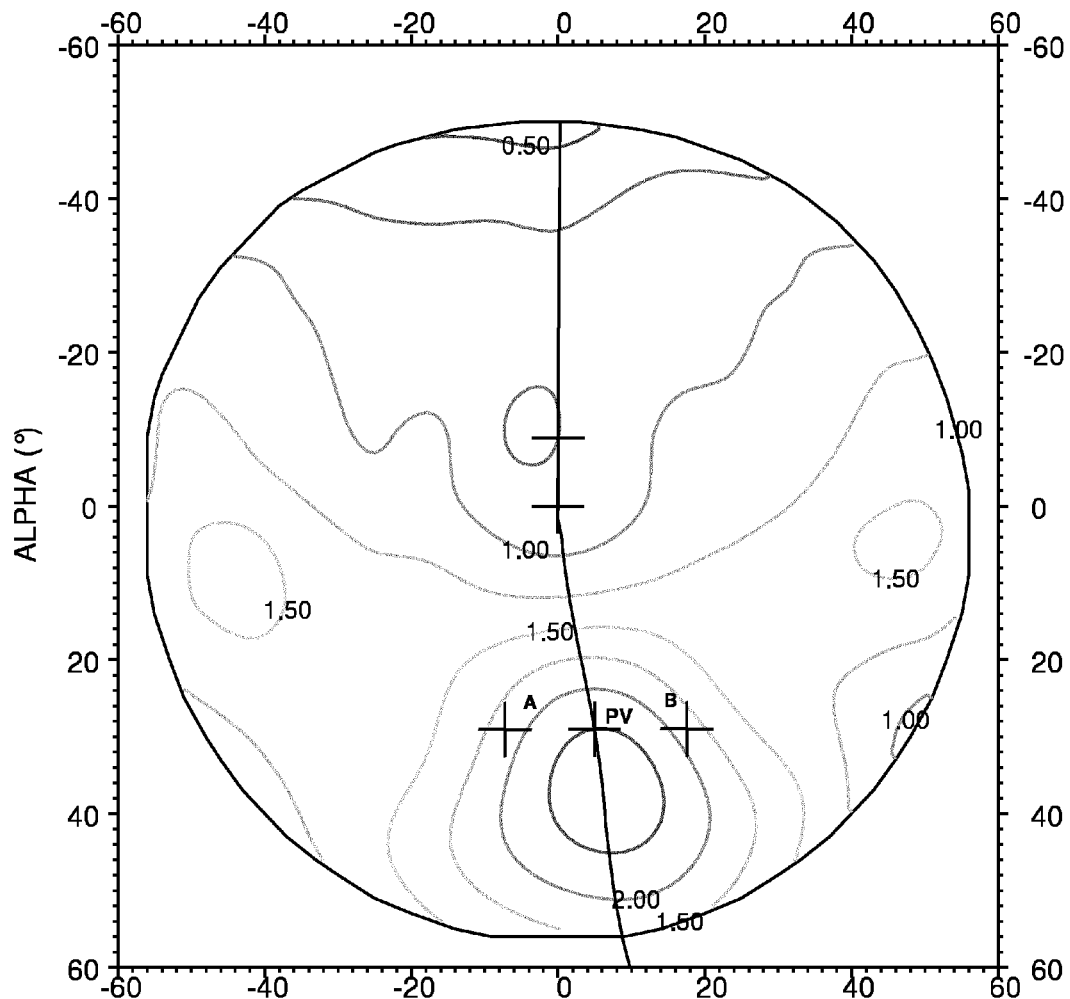
Figure 20:
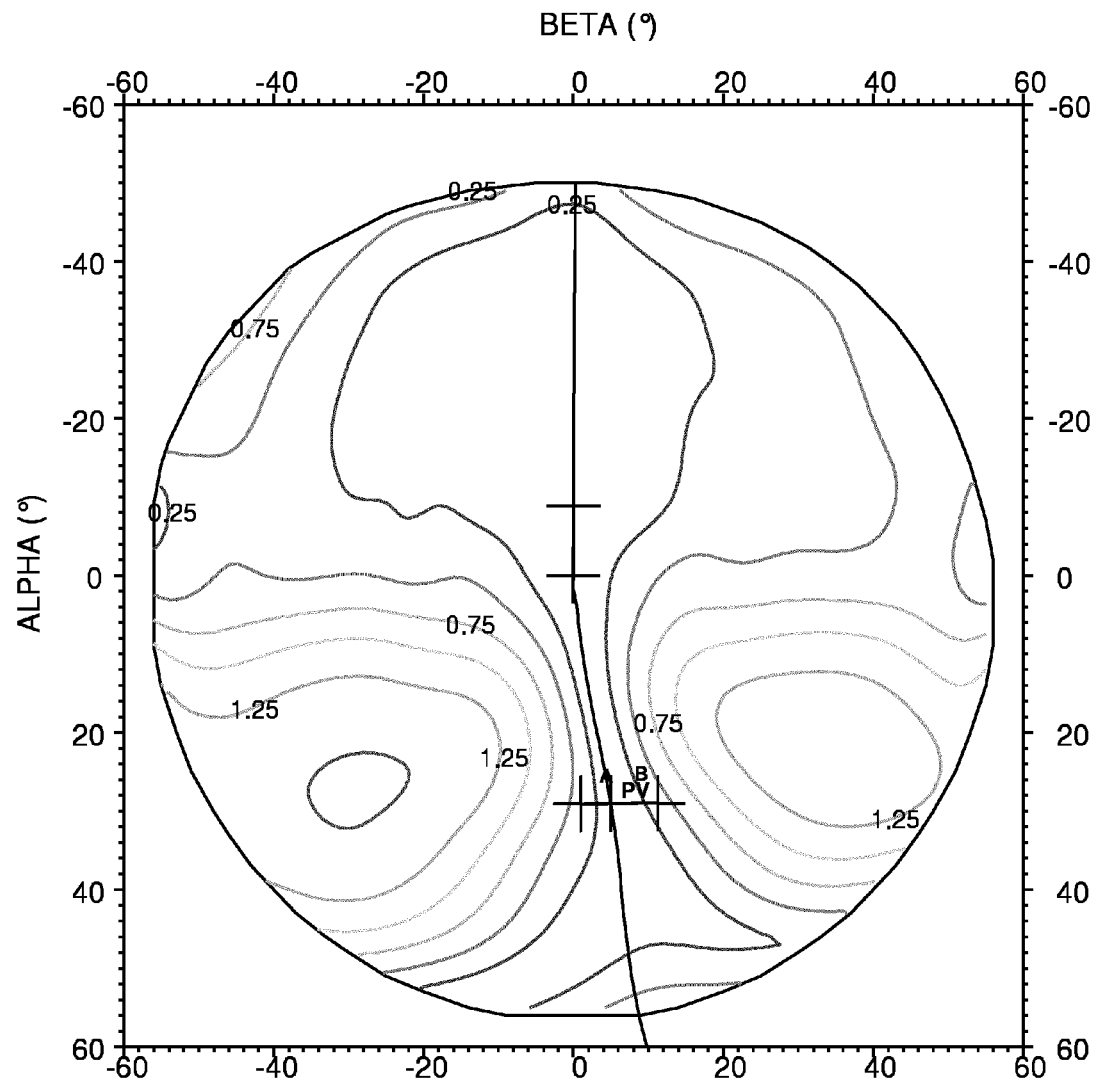

FIGS. 19 and 20 give optical characteristics (refractive power and resulting astigmatism) of the right-eye lens LENS1 of the pair.

Figure 21:
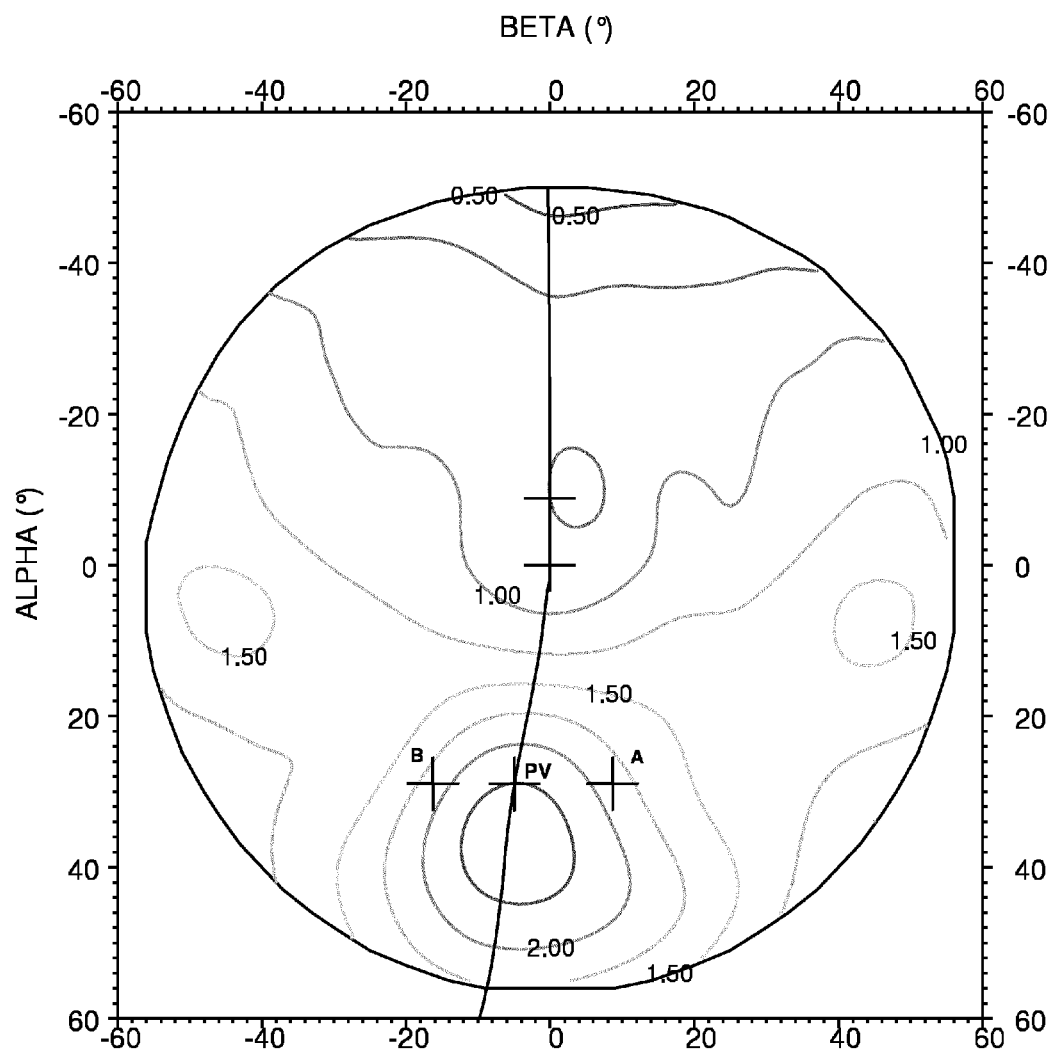
Figure 22:
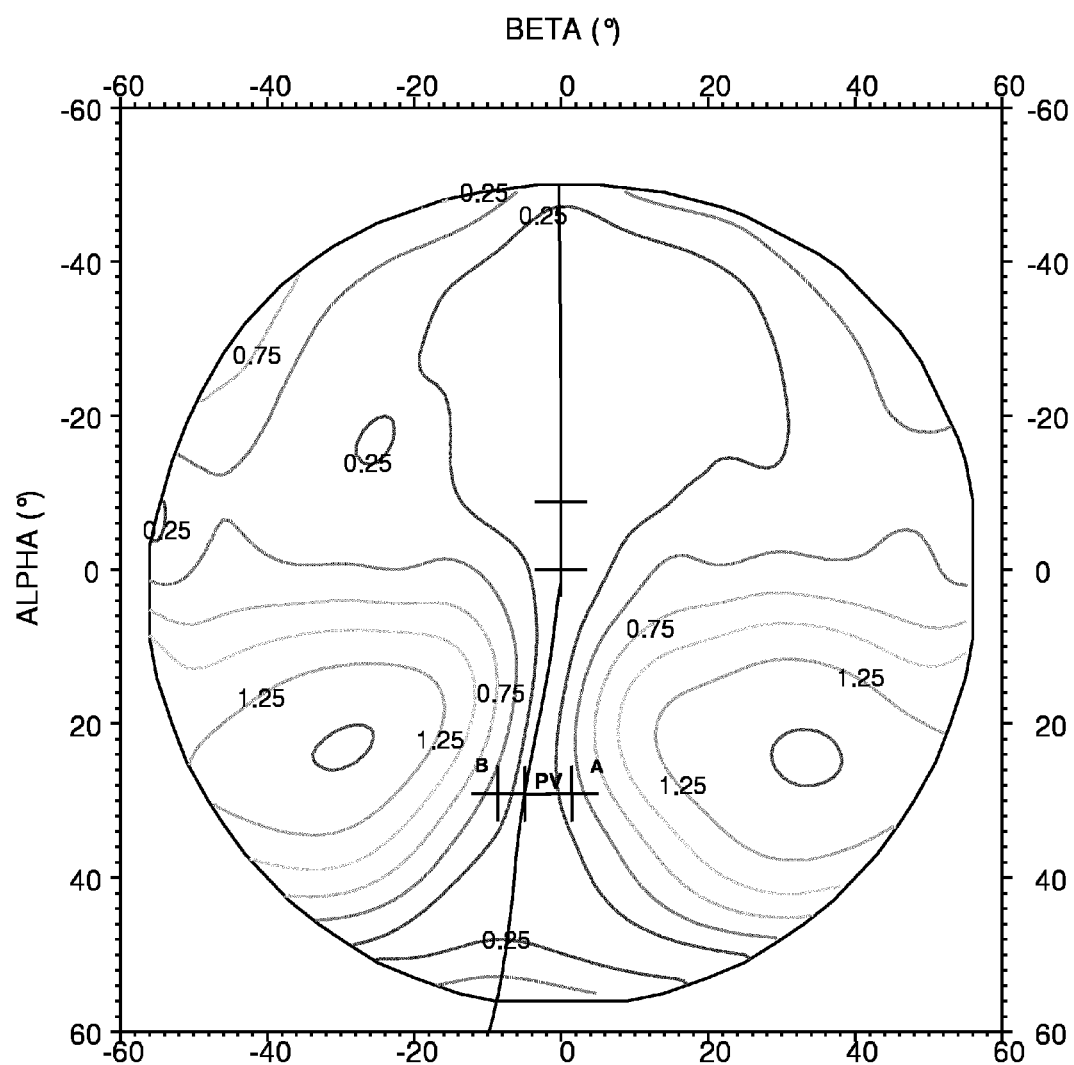

FIGS. 21 and 22 give optical characteristics (refractive power and resulting astigmatism) of the left-eye lens LENS2 of the pair.

On FIG. 19:

Point PV is located at $\alpha_{PVR}=29.0°$ and $\beta_{PVR}=5.0°$

Point PV is located on the isometric curve corresponding to a power value:

$P=0.75+100\%*1.5=2.25\delta$

On FIG. 20:

point PV is located at $\alpha_{PVR}=29.0°$ and $\beta_{PVR}=5.0°$
point A is located at $\alpha_{AR}=\alpha_{PVR}=29.0°$ and $\beta_{AR}=1.3°$
point B is located at $\alpha_{BR}=\alpha_{PVR}=29.0°$ and $\beta_{BR}=11.4°$ The isometric curve connecting points A and B correspond to a resulting astigmatism value:

$Asr=1.5/4=0.375\delta$ $T_{A\_RE}=3.7°$ and $N_{A\_RE}=6.4°$

Then $R_{AR}=-0.27$

On FIG. 21:

Point PV is located at $\alpha_{PVL}=28.9°$ and $\beta_{PVL}=-4.9°$

Point PV is located on the isometric curve corresponding to a power value:

$P=0.75+100\%*1.5=2.25\delta$

On FIG. 22:

point PV is located at $\alpha_{PVL}=28.9°$ and $\beta_{PVL}=-4.9°$
point A is located at $\alpha_{AI}=\alpha_{PVL}=28.9°$ and $\beta_{AL}=1.4°$
point B is located at $\alpha_{BL}=\alpha_{PVL}=28.9°$ and $\beta_{BL}=-8.4°$ The isometric curve connecting points A and B correspond to a resulting astigmatism value:

$Asr=1.5/4=0.375\delta$ $T_{A\_LE}=6.3°$ and $N_{A\_LE}=3.5°$

Then $R_{AL}=0.28$

This pair PAIR3 is intended for a left-handed person. Indeed, the resulting astigmatism ratios are such that:

$R_{AR}\leq 0$ and $R_{AL}\geq 0$

The ratios are further such that $R_{AR}+R_{AL}$ equals substantially to 0 taking into account the tolerance range ($R_{AR}+R_{AL}=0.01$)

The pair of lenses of example 3 thus provides optimal comfort to a left-handed wearer by providing a dissymmetric design in useful zones when the wearer performs near vision tasks.

Example 4

Lens Design Taking Into Account the Reading Inclination

Lenses are determined by taking into account the angle of inclination of the lines of a text in a reading situation.

The angle of inclination θ is determined as described above.

The following relationships are provided, wherein R is anyone of $R_{PL}$, $R_{PR}$, $R_{AL}$, $R_{AR}$ and the sign of R is determined as described herein according to laterality; abs denotes absolute value, LE left eye, RE right eye:

Possible relationships between R and θ at $P_{FV}$+100% A:
  If abs(θ)≤45° then abs($R_{RE}$)=abs($R_{LE}$)=abs(θ)/100
  If abs(θ)>45° then abs($R_{RE}$)=abs($R_{LE}$)=0.45
  For instance:
    If θ=0° then abs($R_{RE}$)=abs($R_{LE}$)=0
    If θ=20° then abs($R_{RE}$)=abs($R_{LE}$)=0.20
Relationship between R and θ at $P_{FV}$+85% A:
  If abs(θ)≤45° then abs($R_{RE}$)=abs($R_{LE}$)=abs(θ)/133
  If abs(θ)>45° then abs($R_{RE}$)=abs($R_{LE}$)=0.34
  For instance:
    If θ=0° then abs($R_{RE}$)=abs($R_{LE}$)=0
    If θ=20° then abs($R_{RE}$)=abs($R_{LE}$)=0.15

Example 5

Lens Design Taking Into Account Head-Eye Behaviour

Lenses are determined by taking into account head/eye behaviour. A value of Gain is determined as described above: Gain=(head angle)/(target angle).

Example 5.1

Relationship Between Gain and Value of Ratios R

In this embodiment, the half-width fields are modified as a function of the Gain, namely the modified temporal (respectively nasal) half-width field is proportional to the unmodified temporal (respectively nasal) half-width field: T'=k*T, wherein T can be either for refractive power or for the module of resulting astigmatism, each for either eye (respectively N'=k*N). T is selected from $T_{P\_LE}$, $T_{P\_RE}$, $T_{A\_LE}$ and $T_{A\_RE}$. N is selected from $N_{A\_LE}$, $N_{A\_RE}$, $N_{P\_RE}$ and $N_{P\_RE}$.

As a consequence, R=(k*T−k*N)/k*(T+N)=(T−N)/(T+N), with R selected from $R_{PL}$, $R_{PR}$, $R_{AL}$, $R_{AR}$. The value of the ratio R does not depend upon the Gain, but the values of the half-width fields do.

For instance, k may be determined as follows: k=−0.4*Gain+1.2.
  If Gain=0, for an eye mover: T'=1.2*T,
  If Gain=1, for a head mover: T'=0.8*T,
In another embodiment, more generally, k=−0.4*Gain+K, wherein K is a constant value of between [1.0-1.2].

Example 5.2

Relationship Between Gain and Value of Ratios R

In this embodiment, other possible values for ratios R are determined as a function of the Gain. The value 0.253 is selected as an average value for the Gain, but other values may be used.

The following relationships are provided below, wherein R is anyone of $R_{PL}$, $R_{PR}$, $R_{AL}$, $R_{AR}$ the sign of R is determined as described herein according to laterality; abs denotes absolute value, LE left eye, RE right eye.

Example 5.2.1

Gain of [0-0.253]

If Gain is between 0 and 0.253, the values for half-width fields are relatively large, and thus the requirement for asymmetry is less pronounced. The absolute values of ratios R may thus be smaller than the absolute values proposed for an 'average' wearer who has a Gain of 0.253.

Thus, for a segmentation between left-handed and right-handed wearers:
  right-handed: abs($R_{RE}$)=abs($R_{LE}$)=0.13 (at $P_{FV}$+85% A or $P_{FV}$+100% A).
  left-handed: abs($R_{RE}$)=abs($R_{LE}$)=0.00 (at $P_{FV}$+85% A or $P_{FV}$+100% A).

For a customization using head/eye behavior and angle of inclination in reading situation, the parameters Gain and θ (°) as defined above are used as follows:
  abs(R)=(abs(θ)/133)*Gain/0.253 (at $P_{FV}$−F85% A) or
  abs(R)=(abs(θ)/100)*Gain/0.253 (at $P_{FV}$+100% A)

Example 5.2.2

Gain of [0.253-1]

Thus for a segmentation: the full extent of laterality is taken into account. It is thus possible to use, for a right-handed wearer, as the absolute value of ratio R, the one obtained for an average inclination of 20°. Conversely, for a left-handed wearer, the ratio is set at the value obtained for an average inclination of 0°.
  right-handed: abs($R_{RE}$)=abs($R_{LE}$)=0.15 or 0.20 ($P_{FV}$+85% A or $P_{FV}$+100% A)
  left-handed: abs($R_{RE}$)=abs($R_{LE}$)=0.00 ($P_{FV}$+85% A or $P_{FV}$+100% A)

For a customization as a function of Gain and 0, the inclination is fully taken into account.

$$abs(R) = \theta/133 \text{ or } \theta/100 (P_{FV}+85\% \text{ A or } P_{FV}+100\% \text{ A}).$$

The invention claimed is:

1. A process for determining a pair of progressive ophthalmic lenses comprising the steps of:
   determining a prescribed far vision mean power ($P_{FV}$) for each lens of the pair;
   determining a prescribed addition (A) for each lens of the pair;
   determining laterality of a wearer;
   defining a temporal side and a nasal side on each lens of the pair;
   defining, on each lens being worn and for each gaze direction, a refractive power ($P_{\alpha,\beta}$) and a module of resulting astigmatism ($Asr_{\alpha,\beta}$), each gaze direction corresponding to a lowering angle (α) and to an azimuth angle (β);
   defining a proximate vision gaze direction ($\alpha_{PV}$, $\beta_{PV}$) for each lens of the pair;
   defining, for each lens of the pair, a temporal half-width field of refractive power ($T_{P\_LE}$, $T_{P\_RE}$) as the angular distance, at constant lowering angle (α), between the proximate vision gaze direction ($\alpha_{PV}$, $\beta_{PV}$) and a gaze direction ($\alpha_{PV}$, $\beta_{TP}$) on the temporal side of the lens where the refractive power reaches the value of the prescribed far vision mean power plus three quarters of the prescribed addition ($P_{FV}$+3/4*A);
   defining, for each lens of the pair, a nasal half-width field of refractive power ($N_{P\_LE}$, $N_{P\_RE}$) as the angular distance, at constant lowering angle (α), between the proximate vision gaze direction ($\alpha_{PV}$, $\beta_{PV}$) and a gaze direction ($\alpha_{PV}$, $\beta_{NP}$) on the nasal side of the lens where the refractive power reaches the value of the prescribed far vision mean power plus three quarters of the prescribed addition ($P_{FV}$+3/4*A);
   defining, for each lens of the pair, a temporal half-width field of module of resulting astigmatism ($T_{A\_LE}$, $T_{A\_RE}$) as the angular distance, at constant lowering angle (α), between the proximate vision gaze direction ($\alpha_{PV}$, $\beta_{PV}$) and a gaze direction ($\alpha_{PV}$, $\beta_{TA}$) on the temporal side of the lens where the module of resulting astigmatism reaches the value of one quarter of the prescribed addition (A/4);

defining, for each lens of the pair, a nasal half-width field of module of resulting astigmatism ($N_{A\_LE}$, $N_{A\_RE}$) as the angular distance, at constant lowering angle ($\alpha$), between the proximate vision gaze direction ($\alpha_{PV}$, $\beta_{PV}$) and a gaze direction ($\alpha_{PV}$, $\beta_{NA}$) on the nasal side of the lens where the module of resulting astigmatism reaches the value of one quarter of the prescribed addition (A/4);

wherein the ratio of the difference over the sum of temporal and nasal half-width fields of refractive power (($T_{P\_LE}-N_{P\_LE})/(T_{P\_LE}+N_{P\_LE})$, $(T_{P\_RE}-N_{P\_RE})/(T_{P\_RE}+N_{P\_RE})$) and/or the ratio of the difference over the sum of temporal and nasal half-width fields of module of resulting astigmatism (($T_{A\_LE}-N_{A\_LE})/(T_{A\_LE}+N_{A\_LE})$, $(T_{A\_RE}-N_{A\_RE})/(T_{A\_RE}+N_{A\_RE})$) are determined for each lens of the pair based on the laterality of the wearer.

2. The process of claim 1, wherein, if the laterality of the wearer is determined to be left-handed, the ratio of the difference over the sum of temporal and nasal half-width fields of refractive power is set to a value less than or equal substantially to 0 for the right-eye lens (($T_{P\_RE}-N_{P\_RE})/(T_{P\_RE}+N_{P\_RE}) \leq 0$) and/or the ratio of the difference over the sum of temporal and nasal half-width fields of module of resulting astigmatism is set to a value less than or equal substantially to 0 for the right-eye lens (($T_{A\_RE}-N_{A\_RE})/(T_{A\_RE}+N_{A\_RE}) \leq 0$), and the ratio of the difference over the sum of temporal and nasal half-width fields of refractive power is set to a value greater than or equal substantially to 0 for the left-eye lens (($T_{P\_LE}-N_{P\_LE})/(T_{P\_LE}+N_{P\_LE}) \geq 0$) and/or the ratio of the difference over the sum of temporal and nasal half-width fields of module of resulting astigmatism is set to a value greater than or equal substantially to 0 for the left-eye lens (($T_{A\_RE}-N_{A\_RE})/(T_{A\_RE}+N_{A\_RE}) \geq 0$); or if the laterality of the wearer is determined to be right-handed, the ratio of the difference over the sum of temporal and nasal half-width fields of refractive power is set to a value greater than or equal substantially to 0 for the right-eye lens (($T_{P\_RE}-N_{P\_RE})/(T_{P\_RE}+N_{P\_RE}) \geq 0$) and/or the ratio of the difference over the sum of temporal and nasal half-width fields of module of resulting astigmatism is set to a value greater than or equal substantially to 0 for the right-eye lens (($T_{A\_RE}-N_{A\_RE})/(T_{A\_RE}+N_{A\_RE}) \geq 0$), and the ratio of the difference over the sum of temporal and nasal half-width fields of refractive power is set to a value less than or equal substantially to 0 for the left-eye lens (($T_{P\_LE}-N_{P\_LE})/(T_{P\_LE}+N_{P\_LE}) \leq 0$) and/or the ratio of the difference over the sum of temporal and nasal half-width fields of module of resulting astigmatism is set to a value less than or equal substantially to 0 for the left-eye lens (($T_{A\_LE}-N_{A\_RE})/(T_{A\_LE}+N_{A\_RE}) \leq 0$).

3. The process of claim 2, wherein the sum of the ratio of the difference over the sum of temporal and nasal half-width fields of refractive power for the right-eye lens and the ratio of the difference over the sum of temporal and nasal half-width fields of refractive power for the left-eye lens is set substantially to 0 (($T_{P\_RE}-N_{P\_RE})/(T_{P\_RE}+N_{P\_RE})+(T_{P\_LE}-N_{P\_LE})/(T_{P\_LE}+N_{P\_LE})=0$).

4. The process of claim 2, wherein the sum of the ratio of the difference over the sum of temporal and nasal half-width fields of module of resulting astigmatism for the right-eye lens and the ratio of the difference over the sum of temporal and nasal half-width fields of module of resulting astigmatism for the left-eye lens is set substantially to 0 (($T_{A\_RE}-N_{A\_RE})/(T_{A\_RE}+N_{A\_RE})+(T_{A\_LE}-N_{A\_RE})/(T_{A\_LE}+N_{A\_RE})=0$).

5. A process for determining a pair of personalized progressive ophthalmic lenses comprising the steps of:

determining a prescribed far vision mean power ($P_{FV}$) for each lens of the pair;

determining a prescribed addition (A) for each lens of the pair;

measuring a useful near vision zone of a wearer and measuring an inclination of the useful near vision zone with respect to an horizontal line;

determining a temporal side and a nasal side on each lens of the pair;

defining, on each lens being worn and for each gaze direction, a refractive power ($P_{\alpha,\beta}$) and module of resulting astigmatism ($Asr_{\alpha,\beta}$), each gaze direction corresponding to a lowering angle ($\alpha$) and to an azimuth angle ($\beta$);

defining a proximate vision gaze direction ($\alpha_{PV}$, $\beta_{PV}$) for each lens of the pair;

defining, for each lens of the pair, a temporal half-width field of refractive power ($T_{P\_LE}$, $T_{P\_RE}$) as the angular distance, at constant lowering angle ($\alpha$), between the proximate vision gaze direction ($\alpha_{PV}$, $\beta_{PV}$) and a gaze direction ($\alpha_{PV}$, $\beta_{TP}$) on the temporal side of the lens where the refractive power reaches the value of the prescribed far vision mean power plus three quarters of the prescribed addition ($P_{FV}+3/4*A$);

defining, for each lens of the pair, a nasal half-width field of refractive power ($N_{P\_LE}$, $N_{P\_RE}$) as the angular distance, at constant lowering angle ($\alpha$), between the proximate vision gaze direction ($\alpha_{PV}$, $\beta_{PV}$) and a gaze direction ($\alpha_{PV}$, $\beta_{NP}$) on the nasal side of the lens where the refractive power reaches the value of the prescribed far vision mean power plus three quarters of the prescribed addition ($P_{FV}+3/4*A$);

defining, for each lens of the pair, a temporal half-width field of module of resulting astigmatism ($T_{A\_LE}$, $T_{A\_RE}$) as the angular distance, at constant lowering angle ($\alpha$), between the proximate vision gaze direction ($\alpha_{PV}$, $\beta_{PV}$) and a gaze direction ($\alpha_{PV}$, $\beta_{TA}$) on the temporal side of the lens where the module of resulting astigmatism reaches the value of one quarter of the prescribed addition (A/4);

defining, for each lens of the pair, a nasal half-width field of module of resulting astigmatism ($N_{A\_RE}$, $N_{A\_RE}$) as the angular distance, at constant lowering angle ($\alpha$), between the proximate vision gaze direction ($\alpha_{PV}$, $\beta_{PV}$) and a gaze direction ($\alpha_{PV}$, $\beta_{NA}$) on the nasal side of the lens where the module of resulting astigmatism reaches the value of one quarter of the prescribed addition (A/4);

wherein the ratio of the difference over the sum of temporal and nasal half-width fields of refractive power (($T_{P\_LE}-N_{P\_LE})/(T_{P\_LE}+N_{P\_LE})$, $(T_{P\_RE}-N_{P\_RE})/(T_{P\_RE}+N_{P\_RE})$) and/or the ratio of the difference over the sum of temporal and nasal half-width fields of module of resulting astigmatism (($T_{A\_LE}-N_{A\_LE})/(T_{A\_LE}+N_{A\_RE})$, $(T_{A\_RE}-N_{A\_RE})/(T_{A\_RE}+N_{A\_RE})$) are determined for each lens of the pair based on the measured inclination of the useful near vision zone of the wearer.

6. The process of claim 1 or 5, further comprising a step of determining a head/eye behaviour of the wearer and wherein the ratio of the difference over the sum of temporal and nasal half-width fields of refractive power (($T_{P\_LE}-N_{P\_LE})/(T_{P\_LE}+N_{P\_LE})$, $(T_{P\_RE}-N_{P\_RE})/(T_{P\_RE}+N_{P\_RE})$) and/or the ratio of the difference over the sum of temporal and nasal half-width fields of module of resulting astigmatism (($T_{A\_LE}-$ $N_{A\_LE})/(T_{A\_LE}+N_{A\_LE})$, $(T_{A\_RE}-N_{A\_RE})/(T_{A\_RE}+N_{A\_RE}))$ are further determined for each lens of the pair based on the head/eye behaviour of the wearer.

7. The process of claim 1 or 5, wherein the proximate vision gaze direction belongs to the meridian line of the lens and is such that the corresponding refractive power is comprised between the prescribed far vision mean power $P_{FV}$ for this lens plus 50% of the addition A prescribed for this lens and the far vision mean power $P_{FV}$ prescribed for this lens plus 125% of the addition prescribed for this lens.

8. The process of claim 1 or 5, wherein the proximate vision gaze direction $(\alpha_{PV}, \beta_{PV})$ is defined, for each lens of the pair, as the gaze direction where the refractive power reaches the prescribed far vision mean power plus 100% of the prescribed addition for said lens of the pair.

9. The process of claim 1 or 5, wherein the proximate vision gaze direction $(\alpha_{PV}, \beta_{PV})$ is defined, for each lens of the pair, as the gaze direction where the refractive power reaches the prescribed far vision mean power plus 85% of the prescribed addition for said lens of the pair.

10. A computer program product comprising one or more stored sequence of instructions that is accessible to a processor and which, when executed by the processor, causes the processor to carry out the steps of claim 1 or 5.

11. A pair of progressive ophthalmic lenses intended for a right-handed wearer, each lens of the pair having a prescribed far vision mean power $(P_{FV})$ and a prescribed addition (A) and comprising a temporal side and a nasal side and a proximate vision control point (PV) defined on the front surface, each lens of the pair having, when being worn and for each gaze direction, a refractive power $(P_{\alpha,\beta})$ and a module of resulting astigmatism $(Asr_{\alpha,\beta})$, each gaze direction corresponding to a lowering angle $(\alpha)$ and to an azimuth angle $(\beta)$,
wherein the right-eye lens has:
a ratio of the difference over the sum of temporal and nasal half-width fields of refractive power value greater than or equal substantially to 0 $((T_{P\_RE}-N_{P\_RE})/(T_{P\_RE}+N_{P\_RE})\geq 0)$; and/or
a ratio of the difference over the sum of temporal and nasal half-width fields of module of resulting astigmatism greater than or equal substantially to 0 $((T_{A\_RE}-N_{A\_RE})/(T_{A\_RE}+N_{A\_RE})\geq 0)$, and
wherein the left-eye lens has:
a ratio of the difference over the sum of temporal and nasal half-width fields of refractive power value less than or equal substantially to 0 lens $((T_{P\_LE}-N_{P\_LE})/(T_{P\_LE}+N_{P\_LE})\leq 0)$;
and/or
a ratio of the difference over the sum of temporal and nasal half-width fields of module of resulting astigmatism less than or equal substantially to 0 $((T_{A\_LE}-N_{A\_RE})/(T_{A\_LE}+N_{A\_RE})\leq 0)$,
with:
a temporal half-width field of refractive power $(T_{P\_LE}, T_{P\_RE})$ defined for each lens of the pair as the angular distance, at constant lowering angle $(\alpha)$, between the proximate vision control point (PV) and the point on the temporal side of the lens where the refractive power reaches the value of the prescribed far vision mean power plus three quarters of the addition $(P_{FV}+3/4*A)$;
a nasal half-width field of refractive power $(N_{P\_LE}, N_{P\_RE})$ defined for each lens of the pair as the angular distance, at constant lowering angle $(\alpha)$, between the proximate vision control point (PV) and the point on the nasal side of the lens where the refractive power reaches the value of the prescribed far vision mean power plus three quarters of the addition $(P_{FV}+3/4*A)$;

a temporal half-width field of module of resulting astigmatism $(T_{A\_LE}, T_{A\_RE})$ defined for each lens of the pair as the angular distance, at constant lowering angle $(\alpha)$, between the proximate vision control point (PV) and the point on the temporal side of the lens where the module of resulting astigmatism reaches the value of one quarter of the addition (A/4);
a nasal half-width field of module of resulting astigmatism $(N_{A\_RE}, N_{A\_RE})$ defined for each lens of the pair as the angular distance, at constant lowering angle $(\alpha)$, between the proximate vision control point (PV) and the point on the nasal side of the lens where the module of resulting astigmatism reaches the value of one quarter of the addition (A/4); and
wherein for respectively each lens of the pair $\Delta \leq 10\%$, with $$\Delta = 100*abs(Max\_Asr\_N - Max\_Asr\_T)/Max(Max\_Asr\_N; Max\_Asr\_T),$$

abs: absolute value,
Max_Asr_N: maximum value of resulting astigmatism found over an area of the lens defined by all gaze directions which are comprised:
within the nasal area of the lens, and
within a zone centered on the gaze direction passing through the PRP (Prism reference point) and containing all gaze directions $(\alpha, \beta)$, respecting the following inequality $(\alpha^2+\beta^2)^{1/2} \leq 40°$,
Max_Asr_T: maximum value of resulting astigmatism found over an area of the lens defined by all gaze directions which are comprised:
within the temporal area of the lens, and
within a zone centered on the gaze direction passing through the PRP (Prism reference point) and containing all gaze directions $(\alpha, \beta)$, respecting the following inequality $(\alpha^2+\beta^2)^{1/2} \leq 40°$, inequality $(\alpha^2+\beta^2)^{1/2} \leq 40°$,
Max(x;y): whichever value of x and y is higher.

12. The pair of lenses of claim 11, wherein the proximate vision control point is defined, for each lens of the pair, as the point on the front surface intersecting the gaze direction where the refractive power reaches the prescribed far vision mean power plus 100% of the prescribed addition for said lens of the pair.

13. The pair of lenses of claim 11, wherein the proximate vision control point is defined, for each lens of the pair, as the point on the front surface intersecting the gaze direction where the refractive power reaches the prescribed far vision mean power plus 85% of the prescribed addition for said lens of the pair.

14. The pair of lenses of claim 11, wherein the sum of the ratio of the difference over the sum of temporal and nasal half-width fields of refractive power for the right-eye lens and the ratio of the difference over the sum of temporal and nasal half-width fields of refractive power for the left-eye lens is substantially equal to 0 $((T_{P\_RE}-N_{P\_RE})/(T_{P\_RE}+N_{P\_RE})+(T_{P\_LE}-N_{P\_LE})/(T_{P\_LE}+N_{P\_LE})=0)$.

15. The pair of lenses of claim 11, wherein the sum of the ratio of the difference over the sum of temporal and nasal half-width fields of module of resulting astigmatism for the right-eye lens and the ratio of the difference over the sum of temporal and nasal half-width fields of module of resulting astigmatism for the left-eye lens is substantially equal to 0 $((T_{A\_RE}-N_{A\_RE})/(T_{A\_RE}+N_{A\_RE})+(T_{A\_LE}-N_{A\_RE})/(T_{A\_LE}+N_{A\_RE})=0)$.

* * * * *